(12) United States Patent
Gantz et al.

(10) Patent No.: US 11,564,879 B2
(45) Date of Patent: *Jan. 31, 2023

(54) SANITIZER COMPOSITION WITH PROBIOTIC/PREBIOTIC ACTIVE INGREDIENT

(71) Applicant: GOJO Industries, Inc., Akron, OH (US)

(72) Inventors: Sarah Gantz, Fairlawn, OH (US); Amanda Copeland, Seville, OH (US); Carrie Anne Zapka, Austintown, OH (US); Jessica Tittl, Akron, OH (US); Venkatesan Padyachi, Kendall Park, NJ (US); Kegui Tian, Hudson, OH (US)

(73) Assignee: GOJO Industries, Inc., Akron, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/819,634

(22) Filed: Nov. 21, 2017

(65) Prior Publication Data

US 2018/0140539 A1  May 24, 2018

Related U.S. Application Data

(60) Provisional application No. 62/425,699, filed on Nov. 23, 2016.

(51) Int. Cl.
| | |
|---|---|
| A61K 8/99 | (2017.01) |
| A61K 35/741 | (2015.01) |
| A61K 35/742 | (2015.01) |
| A61K 9/00 | (2006.01) |
| A61P 11/02 | (2006.01) |
| A61Q 17/00 | (2006.01) |
| A61Q 19/10 | (2006.01) |
| A61K 47/14 | (2017.01) |
| A61K 47/10 | (2017.01) |
| A61K 8/41 | (2006.01) |
| A61K 47/46 | (2006.01) |
| A61K 8/34 | (2006.01) |
| A61K 9/08 | (2006.01) |
| A61K 35/00 | (2006.01) |

(52) U.S. Cl.
CPC .......... *A61K 8/99* (2013.01); *A61K 8/34* (2013.01); *A61K 8/416* (2013.01); *A61K 9/0014* (2013.01); *A61K 9/0043* (2013.01); *A61K 9/08* (2013.01); *A61K 35/741* (2013.01); *A61K 35/742* (2013.01); *A61K 47/10* (2013.01); *A61K 47/14* (2013.01); *A61K 47/46* (2013.01); *A61P 11/02* (2018.01); *A61Q 17/005* (2013.01); *A61Q 19/10* (2013.01); *A61K 2035/11* (2013.01); *A61K 2800/75* (2013.01)

(58) Field of Classification Search
CPC .......... A61K 8/99; A61K 8/34; A61K 8/416; A61K 35/741; A61K 35/742; A61K 9/0043; A61Q 17/005; A61Q 19/10
See application file for complete search history.

(56) References Cited

U.S. PATENT DOCUMENTS

| | | |
|---|---|---|
| 5,269,959 A | 12/1993 | Schreibman |
| 5,352,437 A | 10/1994 | Nakagawa et al. |
| 5,453,121 A | 9/1995 | Nicholls et al. |
| 5,942,479 A | 8/1999 | Frankenbach et al. |
| 5,952,278 A | 9/1999 | Mao et al. |
| 5,981,473 A | 11/1999 | Barefoot |
| 6,040,154 A | 3/2000 | Fayolle et al. |
| 6,210,656 B1 | 4/2001 | Touzan |
| 6,221,847 B1 | 4/2001 | Barefoot |
| 6,235,272 B1 | 5/2001 | Greene |
| 6,358,516 B1 | 3/2002 | Harod |
| 6,376,438 B1 | 4/2002 | Rosenberger |
| 6,423,329 B1 | 7/2002 | Sine et al. |
| 6,509,021 B1 | 1/2003 | Weiss et al. |
| 6,673,755 B2 | 1/2004 | Wei et al. |
| 6,733,751 B2 | 5/2004 | Farmer |
| 6,760,331 B1 | 7/2004 | Moussavi et al. |
| 6,797,683 B2 | 9/2004 | Shana'a et al. |
| 6,814,958 B1 | 11/2004 | Sekimoto |
| 6,849,256 B1 | 2/2005 | Farmer |
| 6,905,673 B2 | 6/2005 | Rajaiah et al. |
| 6,924,256 B2 | 8/2005 | Massaro et al. |
| 7,025,955 B2 | 4/2006 | Siddiqui et al. |

(Continued)

FOREIGN PATENT DOCUMENTS

| | | |
|---|---|---|
| BR | PI 201010487 | 10/2013 |
| CN | 101129311 A | 2/2008 |

(Continued)

OTHER PUBLICATIONS

Ohara et al., Journal of Fermentation and Bioengineering, vol. 81, No. 3, 272-274, 1996, (Year: 1996).*
Elshaghbee et al., Frontiers in Microbiology, Original Research, Jan. 2016, vol. 7, Article 47 (Year: 2016).*
Lactic Acid, Skin Deep Cosmetic Database, EWG, 2019 (Year: 2019).*
U.S. Appl. Nos. 15/474,705; 15/475,814; 15/475,938; 15/476,018; 15/476,099; 15/819,230; 15/819,669; 15/819,694 (Year: 2019).*
International Search Report and Written Opinion from PCT/US2017/025326 dated Jun. 9, 2017.

(Continued)

*Primary Examiner* — Ruth A Davis
(74) *Attorney, Agent, or Firm* — Calfee, Halter & Griswold LLP

(57) ABSTRACT

A sanitizing composition for restoring skin's natural balance of bacteria and/or increasing the production and/or activity of antimicrobial peptides is provided. The sanitizing composition includes about 0.005 wt. % to 15.0 wt. % of an active ingredient that is one or more of a probiotic, probiotic derivative, prebiotic, and a prebiotic derivative and at least one compound that delivers a sanitizing effect.

8 Claims, 7 Drawing Sheets

(56) References Cited

U.S. PATENT DOCUMENTS

| | | |
|---|---|---|
| 7,070,814 B2 | 7/2006 | Qazi et al. |
| 7,198,780 B2 | 4/2007 | Dicianna |
| 7,241,452 B2 | 7/2007 | Veeger et al. |
| 7,429,292 B2 | 9/2008 | McIntosh et al. |
| 7,452,545 B2 | 11/2008 | Yu |
| 7,494,661 B2 | 2/2009 | Sanders |
| 7,507,402 B1 | 3/2009 | Ganeden |
| 7,510,734 B2 | 3/2009 | Sullivan et al. |
| 7,514,105 B2 | 4/2009 | Qazi et al. |
| 7,517,852 B2 | 4/2009 | Walsh et al. |
| 7,541,042 B2 | 6/2009 | Farmer et al. |
| 7,547,527 B2 | 6/2009 | Baur |
| 7,560,125 B2 | 7/2009 | Ananthapadmanabhan et al. |
| 7,611,882 B2 | 11/2009 | Bjørnvad et al. |
| 7,612,027 B2 | 11/2009 | Grasha et al. |
| 7,618,801 B2 | 11/2009 | Jones et al. |
| 7,632,527 B2 | 12/2009 | Jochim et al. |
| 7,651,680 B2 | 1/2010 | Breton et al. |
| 7,666,824 B2 | 2/2010 | Krzysik et al. |
| 7,713,726 B2 | 5/2010 | Farmer |
| 7,758,878 B2 | 7/2010 | Scimeca et al. |
| 7,776,346 B2 | 8/2010 | O'Connor et al. |
| 7,803,746 B2 | 9/2010 | Luu et al. |
| 7,820,420 B2 | 10/2010 | Whitlock |
| 7,824,665 B2 | 11/2010 | Miyamoto et al. |
| 7,910,143 B2 | 3/2011 | Kvist et al. |
| 7,928,087 B2 | 4/2011 | Fack et al. |
| 7,939,107 B2 | 5/2011 | Pleva |
| 8,034,385 B2 | 10/2011 | Golz-Berner et al. |
| 8,067,351 B2 | 11/2011 | Holerca et al. |
| 8,080,258 B2 | 12/2011 | Rothman |
| 8,084,409 B2 | 12/2011 | Lucka et al. |
| 8,088,174 B2 | 1/2012 | Neplaz et al. |
| 8,097,573 B2 | 1/2012 | Lutrario et al. |
| 8,101,214 B2 | 1/2012 | Park et al. |
| 8,114,658 B2 | 2/2012 | Muroyama et al. |
| 8,119,583 B2 | 2/2012 | Day et al. |
| 8,124,573 B2 | 2/2012 | Focht et al. |
| 8,137,706 B2 | 3/2012 | Al-Ghazzewi et al. |
| 8,173,143 B2 | 5/2012 | Tecco |
| 8,222,020 B2 | 7/2012 | Brusk et al. |
| 8,236,744 B2 | 8/2012 | Boyke et al. |
| 8,246,946 B2 | 8/2012 | Cobb et al. |
| 8,257,753 B2 | 9/2012 | Dal Farra et al. |
| 8,283,136 B2 | 10/2012 | Tagg et al. |
| 8,318,659 B2 | 11/2012 | Lowe et al. |
| 8,329,672 B2 | 12/2012 | Prous et al. |
| 8,333,954 B2 | 12/2012 | Seidling et al. |
| 8,337,915 B2 | 12/2012 | Aburdeineh |
| 8,349,803 B2 | 1/2013 | Dal Farra et al. |
| 8,361,450 B2 | 1/2013 | Johnson et al. |
| 8,377,679 B2 | 2/2013 | Baur et al. |
| 8,420,627 B2 | 4/2013 | Guthery |
| 8,455,411 B2 | 6/2013 | Kilthau et al. |
| 8,481,299 B2 | 7/2013 | Gueniche |
| 8,506,952 B2 | 8/2013 | Minbiole et al. |
| 8,575,083 B2 | 11/2013 | Bettiol et al. |
| 8,586,067 B2 | 11/2013 | Okamoto et al. |
| 8,697,055 B2 | 4/2014 | Farmer |
| 8,753,654 B2 | 6/2014 | Narula et al. |
| 8,753,861 B2 | 6/2014 | Cascao-Pereira et al. |
| 8,778,863 B2 | 7/2014 | Pipko |
| 8,779,927 B2 | 7/2014 | Bell et al. |
| 8,785,171 B2 | 7/2014 | Souter et al. |
| 8,801,864 B2 | 8/2014 | Brooke |
| 8,815,538 B2 | 8/2014 | Lanzalaco et al. |
| 8,821,854 B2 | 9/2014 | Farmer et al. |
| 8,822,179 B2 | 9/2014 | Preston, III et al. |
| 8,834,855 B2 | 9/2014 | Johnsen |
| 8,859,627 B2 | 10/2014 | Found |
| 8,877,259 B2 | 11/2014 | Florence et al. |
| 8,951,775 B2 | 2/2015 | Castiel et al. |
| 8,956,624 B2 | 2/2015 | Schnittger et al. |
| 8,993,006 B2 | 3/2015 | Hines et al. |
| 8,999,399 B2 | 4/2015 | Lisowsky et al. |
| 9,062,215 B2 | 6/2015 | Bravo et al. |
| 9,096,821 B1 | 8/2015 | Hope et al. |
| 9,107,920 B2 | 8/2015 | Olsen |
| 9,109,189 B2 | 8/2015 | Perez-Prat Vinuesa et al. |
| 9,125,768 B2 | 9/2015 | Husmark et al. |
| 9,133,417 B2 | 9/2015 | Tajmamet et al. |
| 9,198,852 B2 | 12/2015 | Burt et al. |
| 9,220,736 B2 | 12/2015 | Farmer et al. |
| 9,233,062 B2 | 1/2016 | Florence et al. |
| 9,248,206 B2 | 2/2016 | Brown et al. |
| 9,265,708 B2 | 2/2016 | Yumioka et al. |
| 9,301,982 B2 | 4/2016 | Lefkowitz et al. |
| 10,874,700 B2 * | 12/2020 | Gantz ................ A61K 35/742 |
| 2002/0076422 A1 | 6/2002 | Shah et al. |
| 2004/0243076 A1 | 12/2004 | Husmark et al. |
| 2005/0137102 A1 | 6/2005 | Shoaf |
| 2005/0271595 A1 | 12/2005 | Brown |
| 2006/0140899 A1 | 6/2006 | Koenig et al. |
| 2006/0171936 A1 | 8/2006 | Gueniche et al. |
| 2006/0204466 A1 | 9/2006 | Littau et al. |
| 2006/0210499 A1 | 9/2006 | Hoeffkes |
| 2006/0276369 A1 | 12/2006 | Levecke et al. |
| 2006/0278255 A1 | 12/2006 | Drogue et al. |
| 2007/0020213 A1 | 1/2007 | Tamarkin et al. |
| 2007/0027119 A1 | 2/2007 | Ahmed et al. |
| 2007/0053863 A1 | 3/2007 | Lee |
| 2007/0154411 A1 | 7/2007 | Barth |
| 2008/0045491 A1 | 2/2008 | Fitchmun |
| 2008/0095731 A1 | 4/2008 | Mitra |
| 2008/0107699 A1 | 5/2008 | Spigelman et al. |
| 2008/0112907 A1 | 5/2008 | Chan et al. |
| 2008/0124286 A1 | 5/2008 | Lisson |
| 2008/0139432 A1 | 6/2008 | Peffly et al. |
| 2008/0160043 A1 | 7/2008 | Kim et al. |
| 2008/0193406 A1 | 8/2008 | Rull Prous et al. |
| 2008/0206211 A1 | 8/2008 | Gueniche |
| 2008/0206214 A1 | 8/2008 | Farmer |
| 2008/0226603 A1 | 9/2008 | Al-Ghazzewi et al. |
| 2008/0226756 A1 | 9/2008 | Willemin et al. |
| 2008/0233075 A1 | 9/2008 | Sokolinsky et al. |
| 2008/0233091 A1 | 9/2008 | Ross et al. |
| 2008/0233104 A1 | 9/2008 | Farmer |
| 2008/0241226 A1 | 10/2008 | Abeln et al. |
| 2008/0241263 A1 | 10/2008 | Prous et al. |
| 2008/0247960 A1 | 10/2008 | Yuan |
| 2008/0247993 A1 | 10/2008 | Reindl et al. |
| 2008/0255249 A1 | 10/2008 | Hellwege et al. |
| 2008/0261916 A1 | 10/2008 | Jaszberenyi et al. |
| 2008/0268024 A1 | 10/2008 | Rull Prous et al. |
| 2008/0293669 A1 | 11/2008 | Moriya et al. |
| 2009/0017147 A1 | 1/2009 | Lintner et al. |
| 2009/0022700 A1 | 1/2009 | Cassin et al. |
| 2009/0022819 A1 | 1/2009 | Gueniche et al. |
| 2009/0028805 A1 | 1/2009 | Gueniche et al. |
| 2009/0035294 A1 | 2/2009 | Mahe et al. |
| 2009/0060962 A1 | 3/2009 | Castiel et al. |
| 2009/0068150 A1 | 3/2009 | Park et al. |
| 2009/0068160 A1 | 3/2009 | Castiel et al. |
| 2009/0068161 A1 | 3/2009 | Gueniche et al. |
| 2009/0068219 A1 | 3/2009 | Elie et al. |
| 2009/0074735 A1 | 3/2009 | Joshi |
| 2009/0081143 A1 | 3/2009 | Mammone et al. |
| 2009/0099129 A1 | 4/2009 | Meuser et al. |
| 2009/0123448 A1 | 5/2009 | Bozonnet et al. |
| 2009/0130073 A1 | 5/2009 | Reindl et al. |
| 2009/0136604 A1 | 5/2009 | Breton et al. |
| 2009/0142375 A1 | 6/2009 | Vidal et al. |
| 2009/0143714 A1 | 6/2009 | Millikin et al. |
| 2009/0156563 A1 | 6/2009 | Baschong et al. |
| 2009/0175911 A1 | 7/2009 | Cutting et al. |
| 2009/0180970 A1 | 7/2009 | Tamarkin et al. |
| 2009/0186126 A1 | 7/2009 | Farmer et al. |
| 2009/0202705 A1 | 8/2009 | Meuser et al. |
| 2009/0214497 A1 | 8/2009 | Park et al. |
| 2009/0214501 A1 | 8/2009 | Knapp et al. |
| 2009/0232785 A1 | 9/2009 | Breton et al. |
| 2009/0232892 A1 | 9/2009 | Yamasaki et al. |
| 2009/0232942 A1 | 9/2009 | Degre et al. |
| 2009/0238782 A1 | 9/2009 | Vacher et al. |

(56) References Cited

U.S. PATENT DOCUMENTS

| | | |
|---|---|---|
| 2009/0252775 A1 | 10/2009 | Arndt et al. |
| 2009/0297482 A1 | 12/2009 | Dicks et al. |
| 2009/0305387 A1 | 12/2009 | Farmer |
| 2009/0317370 A1 | 12/2009 | Lang et al. |
| 2010/0003292 A1 | 1/2010 | Gautier et al. |
| 2010/0021532 A1 | 1/2010 | Rao et al. |
| 2010/0022660 A1 | 1/2010 | Wegner |
| 2010/0030172 A1 | 2/2010 | Husmark et al. |
| 2010/0040710 A1 | 2/2010 | Perrier et al. |
| 2010/0055081 A1 | 3/2010 | Richelle et al. |
| 2010/0086520 A1 | 4/2010 | Reindl et al. |
| 2010/0086528 A1 | 4/2010 | Olofsson |
| 2010/0113372 A1 | 5/2010 | Park et al. |
| 2010/0119613 A1 | 5/2010 | Gruber et al. |
| 2010/0120710 A1 | 5/2010 | Watanabe et al. |
| 2010/0121304 A1 | 5/2010 | Zhou et al. |
| 2010/0158988 A1 | 6/2010 | Redmond et al. |
| 2010/0159028 A1 | 6/2010 | Shultz |
| 2010/0190872 A1 | 7/2010 | Sedmak |
| 2010/0196295 A1 | 8/2010 | Alvarado |
| 2010/0197551 A1 | 8/2010 | Bettiol et al. |
| 2010/0197552 A1 | 8/2010 | Koyuncu et al. |
| 2010/0197553 A1 | 8/2010 | Barnabas et al. |
| 2010/0197554 A1 | 8/2010 | Koyuncu et al. |
| 2010/0198177 A1 | 8/2010 | Yahiaoui et al. |
| 2010/0209407 A1 | 8/2010 | Pain et al. |
| 2010/0216892 A1 | 8/2010 | Schmaus |
| 2010/0221226 A1 | 9/2010 | Aubert-Jacquin et al. |
| 2010/0226892 A1 | 9/2010 | Gueniche |
| 2010/0233128 A1 | 9/2010 | Panasenko |
| 2010/0254948 A1 | 10/2010 | Giuliani et al. |
| 2010/0260809 A1 | 10/2010 | Valentova et al. |
| 2010/0272839 A1 | 10/2010 | Gueniche et al. |
| 2010/0278793 A1 | 11/2010 | Gueniche et al. |
| 2010/0291049 A1 | 11/2010 | Izawa et al. |
| 2010/0303931 A1 | 12/2010 | Feltin et al. |
| 2010/0317743 A1 | 12/2010 | Macinga et al. |
| 2010/0330013 A1 | 12/2010 | O'Connell et al. |
| 2010/0330128 A1 | 12/2010 | Kang et al. |
| 2010/0331429 A1 | 12/2010 | Lorant |
| 2011/0002891 A1 | 1/2011 | Minbiole et al. |
| 2011/0027221 A1 | 2/2011 | Fu et al. |
| 2011/0034393 A1 | 2/2011 | Justen et al. |
| 2011/0038840 A1 | 2/2011 | Chen et al. |
| 2011/0052514 A1 | 3/2011 | Justen et al. |
| 2011/0052519 A1 | 3/2011 | Carreno et al. |
| 2011/0064835 A1 | 3/2011 | Martin et al. |
| 2011/0117032 A1 | 5/2011 | Gilding |
| 2011/0143007 A1 | 6/2011 | Stengel |
| 2011/0150952 A1 | 6/2011 | Simonnet et al. |
| 2011/0151009 A1 | 6/2011 | Golz-Berner et al. |
| 2011/0177140 A1 | 7/2011 | Voegeli et al. |
| 2011/0182861 A1 | 7/2011 | Castiel et al. |
| 2011/0182863 A1 | 7/2011 | Jia |
| 2011/0189133 A1 | 8/2011 | Tagg et al. |
| 2011/0189343 A1 | 8/2011 | Hasegawa et al. |
| 2011/0201536 A1 | 8/2011 | O'Connell et al. |
| 2011/0223219 A1 | 9/2011 | Dao et al. |
| 2011/0262558 A1 | 10/2011 | Huckfeldt et al. |
| 2011/0274676 A1 | 11/2011 | Farmer et al. |
| 2011/0280850 A1 | 11/2011 | Starr et al. |
| 2011/0294731 A1 | 12/2011 | Torfi |
| 2011/0301118 A1 | 12/2011 | Koenig |
| 2012/0003178 A1 | 1/2012 | Koenic |
| 2012/0009132 A1 | 1/2012 | Tholath et al. |
| 2012/0027735 A1 | 2/2012 | Beland et al. |
| 2012/0034190 A1 | 2/2012 | Apt et al. |
| 2012/0082657 A1 | 4/2012 | Yim |
| 2012/0107290 A1 | 5/2012 | Prioult et al. |
| 2012/0114776 A1 | 5/2012 | Feher |
| 2012/0121522 A1 | 5/2012 | Gruber et al. |
| 2012/0128755 A1 | 5/2012 | Gruber et al. |
| 2012/0156144 A1 | 6/2012 | Tamarkin et al. |
| 2012/0156171 A1 | 6/2012 | Breton et al. |
| 2012/0164087 A1 | 6/2012 | Carter |
| 2012/0164121 A1 | 6/2012 | Paufique |
| 2012/0165290 A1 | 6/2012 | Dijkhuizen et al. |
| 2012/0178731 A1 | 7/2012 | Guthery |
| 2012/0184626 A1 | 7/2012 | Guerra-Vega |
| 2012/0225029 A1 | 9/2012 | Al-Qahtani |
| 2012/0225035 A1 | 9/2012 | Suchanek et al. |
| 2012/0237494 A1 | 9/2012 | Daly et al. |
| 2012/0251512 A1 | 10/2012 | Farmer et al. |
| 2012/0251625 A1 | 10/2012 | Tasiemski et al. |
| 2012/0258126 A1 | 10/2012 | Scholler et al. |
| 2012/0258152 A1 | 10/2012 | De Heinrich et al. |
| 2012/0263758 A1 | 10/2012 | Chinachoti et al. |
| 2012/0294841 A1 | 11/2012 | Gueniche et al. |
| 2012/0301452 A1 | 11/2012 | Gueniche et al. |
| 2012/0322758 A1 | 12/2012 | Kim et al. |
| 2013/0017239 A1 | 1/2013 | Viladot Petit et al. |
| 2013/0034596 A1 | 2/2013 | Apert et al. |
| 2013/0039862 A1 | 2/2013 | Malle et al. |
| 2013/0045197 A1 | 2/2013 | Chavan et al. |
| 2013/0052185 A1 | 2/2013 | Kim et al. |
| 2013/0053422 A1 | 2/2013 | Edmonds et al. |
| 2013/0071470 A1 | 3/2013 | Aburdeineh |
| 2013/0089524 A1 | 4/2013 | Petit et al. |
| 2013/0115317 A1 | 5/2013 | Charbonneau et al. |
| 2013/0129653 A1 | 5/2013 | Castiel et al. |
| 2013/0149257 A1 | 6/2013 | Giori et al. |
| 2013/0230609 A1 | 9/2013 | Modak |
| 2013/0251695 A1 | 9/2013 | Farmer et al. |
| 2013/0287708 A1 | 10/2013 | Silberstein et al. |
| 2013/0302298 A1 | 11/2013 | Chevalier et al. |
| 2013/0323335 A1 | 12/2013 | Rozenblat et al. |
| 2014/0004165 A1 | 1/2014 | Novejarque et al. |
| 2014/0004214 A1 | 1/2014 | Kedrowski et al. |
| 2014/0023693 A1 | 1/2014 | Guenzburg et al. |
| 2014/0037688 A1 | 2/2014 | Berkes et al. |
| 2014/0065209 A1 | 3/2014 | Putaala et al. |
| 2014/0065210 A1 | 3/2014 | Koenig et al. |
| 2014/0065218 A1 | 3/2014 | Lang et al. |
| 2014/0073009 A1 | 3/2014 | Joergensen et al. |
| 2014/0079657 A1 | 3/2014 | Resnick et al. |
| 2014/0094525 A1 | 4/2014 | Snyder et al. |
| 2014/0099270 A1 | 4/2014 | Fu et al. |
| 2014/0186409 A1 | 7/2014 | Lang et al. |
| 2014/0193888 A1 | 7/2014 | Souter et al. |
| 2014/0205651 A1 | 7/2014 | Forsgren Brusk et al. |
| 2014/0242198 A1 | 8/2014 | Modak et al. |
| 2014/0243423 A1 | 8/2014 | Gurge |
| 2014/0271877 A1 | 9/2014 | Wilmott et al. |
| 2014/0301994 A1 | 10/2014 | Klapper |
| 2014/0308258 A1 | 10/2014 | Matthews |
| 2014/0308375 A1 | 10/2014 | Willimann |
| 2014/0322151 A1 | 10/2014 | Fricke et al. |
| 2014/0335043 A1 | 11/2014 | Chon et al. |
| 2014/0342437 A1 | 11/2014 | Barnes et al. |
| 2014/0349375 A1 | 11/2014 | Benjamin et al. |
| 2014/0356295 A1 | 12/2014 | Gerardi et al. |
| 2014/0356296 A1 | 12/2014 | Stoer |
| 2014/0364509 A1 | 12/2014 | Wegner et al. |
| 2015/0024072 A1 | 1/2015 | Chon et al. |
| 2015/0024073 A1 | 1/2015 | Chon et al. |
| 2015/0024074 A1 | 1/2015 | Batchvarova et al. |
| 2015/0024077 A1 | 1/2015 | Batchvarova et al. |
| 2015/0044317 A1 | 2/2015 | Farmer et al. |
| 2015/0073051 A1 | 3/2015 | Cohen et al. |
| 2015/0079040 A1 | 3/2015 | O'Neill et al. |
| 2015/0093462 A1 | 4/2015 | Yarosh et al. |
| 2015/0148309 A1 | 5/2015 | Damor |
| 2015/0202136 A1 | 7/2015 | Lanzalaco et al. |
| 2015/0209392 A1 | 7/2015 | Song et al. |
| 2015/0258003 A1 | 9/2015 | Copeland et al. |
| 2015/0265666 A1 | 9/2015 | Modak et al. |
| 2015/0290273 A1 | 10/2015 | Botto et al. |
| 2015/0305343 A1 | 10/2015 | Burke et al. |
| 2015/0320038 A1 | 11/2015 | Marthaler |
| 2015/0320809 A1 | 11/2015 | Carpenter et al. |
| 2015/0353870 A1 | 12/2015 | Lant |
| 2015/0374607 A1 | 12/2015 | Lanzalaco et al. |
| 2016/0000845 A1 | 1/2016 | Olsen |
| 2016/0008412 A1 | 1/2016 | Putaala et al. |

(56) References Cited

U.S. PATENT DOCUMENTS

| | | | |
|---|---|---|---|
| 2016/0040119 A1 | 2/2016 | Hashman | |
| 2016/0053240 A1 | 2/2016 | Olinski et al. | |
| 2016/0074312 A1 | 3/2016 | Msika et al. | |
| 2016/0074460 A1 | 3/2016 | Deo | |
| 2016/0158444 A1 | 6/2016 | Guillermo et al. | |
| 2016/0279075 A1 | 9/2016 | Redmond | |
| 2017/0281660 A1 | 10/2017 | Zapka | |
| 2017/0281694 A1 | 10/2017 | Gantz | |
| 2017/0281695 A1 | 10/2017 | Gantz | |
| 2017/0281717 A1 | 10/2017 | Hudson | |
| 2017/0281718 A1 | 10/2017 | Hudson | |
| 2018/0140527 A1 | 5/2018 | Hudson | |
| 2018/0140540 A1 | 5/2018 | Gantz | |
| 2018/0140545 A1 | 5/2018 | Hudson | |

FOREIGN PATENT DOCUMENTS

| | | |
|---|---|---|
| CN | 102000009 B | 6/2012 |
| CN | 103599051 A | 2/2014 |
| CN | 104274357 A | 1/2015 |
| CN | 104666285 A | 6/2015 |
| CN | 104862098 A | 8/2015 |
| CN | 104997674 A | 10/2015 |
| CN | 105106062 A | 12/2015 |
| CN | 105482915 A | 4/2016 |
| CN | 105796377 A | 7/2016 |
| DE | 102004011968 A1 | 9/2005 |
| DE | 102011009798 A1 | 8/2012 |
| DE | 102012002592 A1 | 8/2013 |
| DE | 102013225844 A1 | 6/2015 |
| EP | 1060745 A2 | 12/2000 |
| EP | 2081606 | 2/2002 |
| EP | 1594554 B1 | 7/2004 |
| EP | 1736537 A1 | 12/2006 |
| EP | 1438072 B1 | 5/2008 |
| EP | 1920774 A1 | 5/2008 |
| EP | 1911494 A3 | 7/2008 |
| EP | 1965765 A2 | 9/2008 |
| EP | 1344528 B1 | 10/2008 |
| EP | 1455802 B1 | 10/2008 |
| EP | 1778258 B1 | 1/2009 |
| EP | 2019133 A1 | 1/2009 |
| EP | 1602377 A4 | 6/2009 |
| EP | 1296701 B1 | 9/2009 |
| EP | 1311238 B1 | 10/2009 |
| EP | 1529097 B1 | 10/2009 |
| EP | 1787651 B1 | 2/2010 |
| EP | 1301078 B1 | 3/2010 |
| EP | 1672015 B1 | 11/2010 |
| EP | 2305212 A1 | 4/2011 |
| EP | 2308566 A1 | 4/2011 |
| EP | 1353631 B1 | 9/2011 |
| EP | 2364712 A1 | 9/2011 |
| EP | 2430135 | 3/2012 |
| EP | 2441433 A1 | 4/2012 |
| EP | 1739095 A4 | 8/2012 |
| EP | 2556823 A2 | 2/2013 |
| EP | 2929873 A1 | 10/2015 |
| FR | 2908306 A1 | 5/2008 |
| FR | 2912055 A1 | 8/2008 |
| FR | 2916634 A1 | 12/2008 |
| FR | 2930155 A1 | 10/2009 |
| FR | 29387682937548 A1 | 4/2010 |
| FR | 2938768 A1 | 5/2010 |
| FR | 2940098 A1 | 6/2010 |
| FR | 2942720 A1 | 9/2010 |
| FR | 2956818 A1 | 9/2011 |
| FR | 2959126 A1 | 10/2011 |
| FR | 2963560 A3 | 2/2012 |
| FR | 2968990 A1 | 6/2012 |
| FR | 2973381 A1 | 10/2012 |
| FR | 3040624 A1 | 3/2017 |
| GB | 2391476 A | 2/2004 |
| GB | 2466195 A | 6/2010 |
| GB | 2472790 A | 2/2011 |
| JP | H069349 A | 1/1994 |
| JP | H06287106 A | 10/1994 |
| JP | 2000143513 A | 5/2000 |
| JP | 20071786505 A | 7/2007 |
| JP | 2008099632 A | 5/2008 |
| JP | 2008105983 A | 5/2008 |
| JP | 2008179595 A | 8/2008 |
| JP | 2008179601 A | 8/2008 |
| JP | 2008194026 A | 8/2008 |
| JP | 2008212111 A | 9/2008 |
| JP | 2008308478 A | 12/2008 |
| JP | 2009084228 A | 4/2009 |
| JP | 2009143860 A | 7/2009 |
| JP | 2009144165 A | 7/2009 |
| JP | 2009242309 A | 10/2009 |
| JP | 2009292808 A | 12/2009 |
| JP | 2010006757 A | 1/2010 |
| JP | 2010126484 A | 6/2010 |
| JP | 2010132629 A | 6/2010 |
| JP | 2010143885 A | 7/2010 |
| JP | 2010150240 A | 7/2010 |
| JP | 2010270152 A | 12/2010 |
| JP | 2011168520 A | 9/2011 |
| JP | 2011195537 A | 10/2011 |
| JP | 2011195601 A | 10/2011 |
| JP | 2011195843 A | 10/2011 |
| JP | 2012188453 A | 10/2012 |
| KR | 2010130094 A | 12/2010 |
| KR | 2011026237 A | 3/2011 |
| PL | 219328 B1 | 4/2015 |
| WO | 9606153 A2 | 2/1996 |
| WO | 9629867 A2 | 10/1996 |
| WO | 1997049793 A2 | 12/1997 |
| WO | 1998047374 A1 | 10/1998 |
| WO | 2000006116 A1 | 2/2000 |
| WO | 2001013927 A2 | 3/2001 |
| WO | 2002045727 A1 | 6/2002 |
| WO | 2003028738 A2 | 4/2003 |
| WO | 2003086274 A2 | 10/2003 |
| WO | 2004055041 A2 | 7/2004 |
| WO | 2005016364 A1 | 2/2005 |
| WO | 2005027893 A1 | 3/2005 |
| WO | 2006015726 A1 | 2/2006 |
| WO | 2006104403 A1 | 10/2006 |
| WO | 2006118942 A2 | 11/2006 |
| WO | 2008021441 A2 | 2/2008 |
| WO | 2008047908 A1 | 4/2008 |
| WO | 2008015343 A3 | 5/2008 |
| WO | 2008040516 A3 | 5/2008 |
| WO | 2008114376 A1 | 9/2008 |
| WO | 2008146116 A2 | 12/2008 |
| WO | 2008148694 A1 | 12/2008 |
| WO | 2009017463 A2 | 2/2009 |
| WO | 2009031099 A2 | 3/2009 |
| WO | 2009050677 A2 | 4/2009 |
| WO | 2009053564 A2 | 4/2009 |
| WO | 2009066537 A1 | 5/2009 |
| WO | 2009077749 A1 | 6/2009 |
| WO | 2009086614 A1 | 7/2009 |
| WO | 2009087356 A1 | 7/2009 |
| WO | 2009095456 A1 | 8/2009 |
| WO | 2009127057 A1 | 10/2009 |
| WO | 2009141542 A2 | 11/2009 |
| WO | 2009141544 A2 | 11/2009 |
| WO | 2010013182 A1 | 2/2010 |
| WO | 2010061383 A1 | 6/2010 |
| WO | 2010087373 A1 | 8/2010 |
| WO | 2010126414 A1 | 11/2010 |
| WO | 2010128906 A1 | 11/2010 |
| WO | 2010130541 A1 | 11/2010 |
| WO | 2011019668 A1 | 2/2011 |
| WO | 2011029784 A1 | 3/2011 |
| WO | 2011048554 A2 | 4/2011 |
| WO | 2011061144 A2 | 5/2011 |
| WO | 2011064524 A1 | 6/2011 |
| WO | 2011065772 A2 | 6/2011 |
| WO | 2011073437 A2 | 6/2011 |
| WO | 2011117547 A1 | 9/2011 |
| WO | 2011130788 A1 | 10/2011 |

(56) References Cited

FOREIGN PATENT DOCUMENTS

| | | |
|---|---|---|
| WO | 2011157968 A1 | 12/2011 |
| WO | 2011158027 A1 | 12/2011 |
| WO | 2012000960 A1 | 1/2012 |
| WO | 2012000961 A1 | 1/2012 |
| WO | 2012000963 A1 | 1/2012 |
| WO | 2012013764 A2 | 2/2012 |
| WO | 2012013776 A2 | 2/2012 |
| WO | 2012022478 A2 | 2/2012 |
| WO | 2012022773 A1 | 2/2012 |
| WO | 2012049697 A1 | 4/2012 |
| WO | 2012055408 | 5/2012 |
| WO | 2012062895 A1 | 5/2012 |
| WO | 2012067321 A1 | 5/2012 |
| WO | 2012071654 A1 | 6/2012 |
| WO | 2012072951 A1 | 6/2012 |
| WO | 2012076321 A1 | 6/2012 |
| WO | 2012082065 A1 | 6/2012 |
| WO | 2012084701 A2 | 6/2012 |
| WO | 2012107550 A2 | 8/2012 |
| WO | 2012118535 A1 | 9/2012 |
| WO | 2012120290 A2 | 9/2012 |
| WO | 2012129683 | 10/2012 |
| WO | 2012149110 A1 | 11/2012 |
| WO | 2012150269 A1 | 11/2012 |
| WO | 2012152270 A1 | 11/2012 |
| WO | 2012160289 A2 | 11/2012 |
| WO | 2013000717 A2 | 1/2013 |
| WO | 2013050697 A2 | 4/2013 |
| WO | 2013068962 A2 | 5/2013 |
| WO | 2013072322 A1 | 5/2013 |
| WO | 2013073431 A1 | 5/2013 |
| WO | 2013087665 A2 | 6/2013 |
| WO | 2013089720 A1 | 6/2013 |
| WO | 2013100003 A1 | 7/2013 |
| WO | 2013120481 A2 | 8/2013 |
| WO | 2013122931 A2 | 8/2013 |
| WO | 2013130829 A1 | 9/2013 |
| WO | 2013149323 | 10/2013 |
| WO | 2013171343 A2 | 11/2013 |
| WO | 2013188626 | 12/2013 |
| WO | 2013190542 | 12/2013 |
| WO | 2014043304 | 3/2014 |
| WO | 2014044957 A1 | 3/2014 |
| WO | 2014064397 A1 | 5/2014 |
| WO | 2014107572 A1 | 7/2014 |
| WO | 2014131191 A1 | 9/2014 |
| WO | 2014155111 | 10/2014 |
| WO | 2014162125 A1 | 10/2014 |
| WO | 2014197168 A1 | 12/2014 |
| WO | 2015000972 | 1/2015 |
| WO | 2015075440 | 5/2015 |
| WO | 2015089441 | 6/2015 |
| WO | 2015106175 A1 | 7/2015 |
| WO | 2015120100 | 8/2015 |
| WO | 2015124943 | 8/2015 |
| WO | 2015138296 A1 | 9/2015 |
| WO | 2015138479 A1 | 9/2015 |
| WO | 2015143360 | 9/2015 |
| WO | 2015151009 | 10/2015 |
| WO | 2015171899 A1 | 11/2015 |
| WO | 2015185689 | 12/2015 |
| WO | 2015189049 | 12/2015 |
| WO | 2016007314 A1 | 1/2016 |
| WO | 2016161074 A2 | 10/2016 |
| WO | 2016172686 A1 | 10/2016 |
| WO | 2017173236 A1 | 10/2017 |
| WO | 2017173240 A1 | 10/2017 |
| WO | 2017173241 A1 | 10/2017 |
| WO | 2017173242 A1 | 10/2017 |

OTHER PUBLICATIONS

International Search Report and Written Opinion from PCT/US2017/025319 dated Jul. 17, 2017.
International Search Report and Written Opinion from PCT/US2017/025324 dated Jun. 14, 2017.
International Search Report and Written Opinion from PCT/US2017/025323 dated Jun. 27, 2017.
International Search Report and Written Opinion from PCT/US2017/025329 dated Jul. 21, 2017.
Invitation to Pay Additional Fees from PCT/US2017/062766 dated Feb. 26, 2018.
International Search Report and Written Opinion from PCT/US2017/062797 dated Feb. 19, 2018.
International Search Report and Written Opinion from PCT/US2017/062807 dated Mar. 2, 2018.
International Search Report and Written Opinion from PCT/US2017/062784 dated Feb. 22, 2018.
Anonymous, "Ashland Care Specialties Announces Skin's Ecology, an Initiative for Probiotic Effects—Produktneuheiten—SOFW" Retrieved from the Internet: URL: http://www.sofw.com/index/sofw_de/sofw de_produktneuhei ten. html ?naid=5133 retrieved on Jun. 8, 2017] the whole document. Mar. 5, 2013 XP055379410.
Branco, C. et al. "Modulation of Skin Microbiota by Topical Prebiotics", Monographic Supplement Series: Skin Care—Household and Personal Care Today, vol. 10(2) Mar./Apr. 2015, p. 21-27.
Dong Z et al., Composition, Useful for Claning Hair, Comprises Chichona Tree Tincture, Saponin Tincture, Eucalyptus Tincture, Flaxseed Extract, Ethyl Alcohol, and Active Comonent Comprising Vitamin E, Ectoine and Vitamin B5, Clarivate Analytics, vol. 2015, No. 27, Jan. 14, 2015 Abstract.
Fehlbaum P et al., "An Essential Amino Acid Induces Epithelial Beta-Defnsin Expression," Proceedings National Academy of Sciences PNAS, National Academy of Sciences, US, vol. 97, No. 23, Nov. 7, 2000, pp. 12723-12728.
Firas A Al-Bayati, "Antibacterial Activity of *Linum usitati* Ssimum L. Seeds and Active Compound Detection", Rafi Dai N Journal of Science, Mosul University Faculty, IQ, vol. 18, No. 2, Jan. 1, 2007, pp. 27-36.
Gaurav Kaithwas et al., "*Linum usitati* Ssimum (Linseed/Flaxseed) Fixed Oil: Antimicrobial Activity and Efficacy in Bovine Mastitis", Inflammopharmac0logy, Kluwer Academic Publishers, Dordrecht, NL, vol. 19, No. 1, Feb. 1, 2011, pp. 45-52.
Hill et al., The International Scientic Association for Probiotics and Prebiotics Consensus Statement on the Scope and Apprpriate Use of the Term Proboiotic, Expert Consensus Document, Nature Reviews/Gastroenterology & Hepatology, vol. 11, No. 8, Aug. 1, 2015, pp. 506-514.
Hutkins et al., "Prebiotics: Why Definitions Matter," Current Opinion in Biotechnology, vol. 37, Sep. 29, 2015, pp. 1-7.
Jimborean et al. "Use of Essential Oils from Citrus sinensis in the Development of New Type of Yogurt", Bulletin of University of Agricultural Sciences and Veterinary Medicine Cluj-Napoca. Food Science and Technology, vol. 73, No. 1, May 1, 2016.
Kimble et al., "Use of a Fluorometric Microplate Assay to Assess the Activty of Prebiotics and Probiotics Against Uropathogenic *E. coli* Adherence to Human Uroepithelial Cells," FASEB Journal, vol. 29, No. Suppl 1, Apr. 1, 2015, p. 607.9.
Mintel, "Baby's Body Wash" Apr. 2014 XP002777898.
Mintel, "Body Wash" Dec. 2009 XP002777900.
Mintel, "Moisturizing Body Wash" Jan. 2013 XP002777899.
Mintel, "Shower Gel" Jul. 2016 XP002777896.
Mintel, "Shower Gel" Nov. 2014 XP002777897.
Mintel; "Hand Gel" Nov. 2014 XP002777823, retrieved from www.gnpd.com.
Rousseau et al., "Prebiotic Effects of Oligosaccharides on Selected Vaginal Lactobacilli and Pathogenic Microorganisms," Anae London, GB, vol. 11, No. 3, Jun. 1, 2005, pp. 145-153.
Shoaf K et al., "Prebiotic Galactooligosaccharides Reduce Adherence of Enteropathogenic-*Escherichia coli* to Tissue Culture Cells," Infection and Immunity, American Society for Microbiology, vol. 74, No. 12, Dec. 1, 2006, pp. 6920-6928.
Lucera et al., Food Applicatons of Natural Antimicrobial Compounds, Frontiers in Microbiology, vol. 3, pp. 1-13, Aug. 8, 2012.

(56) References Cited

OTHER PUBLICATIONS

Bockmuhl, D. et al. "Prebiotic Cosmetics: An Alternative to Antibacterial Products," Int'l J of Cosmetic Sci., vol. 29, Issue 1, Feb. 13, 2007 Abstract.
Karamac et al., "Antioxidant Activity of Hydrolysates Prepared From Flaxseed Cake Proteins Using Pancreatin," Pol. J. Food Nutr. Sci, 2014, vol. 64, No. 4, pp. 227-233.
Marambe, et al., An In-Vitro Investigation of Selected Biological Activities of Hydrolysed Flaxseed (*Linum usitatissimum* L.) Proteins, J Am Oil Chem Soc, 2008, vol. 85, pp. 1155-1164.
Shim et al., "Flaxseed (*Linum usitatissim* Um L.) Bioactive Compound and Peptide Nomenclature: A Review" Trends in Food Science & Technology, vol. 38, Issue 1, Jul. 2014, pp. 5-20.
Ueda et al., "Topical and Transdermal Drug Products," Pharmacopeial Forum, vol. 35(3); pp. 750-764, May-Jun. 2009.
https://en.wikipedia.org/wiki/Clostridium (Year: 2020).
https://en.wikipedia.org/wiki/Escherichia_coli (Year: 2020).
https://en.wikipedia.org/wiki/Lactobacillus (Year: 2020).
https://en.wikipedia.org/wiki/Saccharomyces (Year: 2020).

\* cited by examiner

SANITIZER COMPOSITION WITH PROBIOTIC/PREBIOTIC ACTIVE INGREDIENT

RELATED APPLICATIONS

This application claims priority to and the benefit of U.S. Provisional Patent Application Ser. No. 62/425,699, entitled "SANITIZER COMPOSITION WITH PROBIOTIC/PREBIOTIC ACTIVE INGREDIENT" and filed Nov. 23, 2016, the entire disclosure of which is incorporated herein by reference.

BACKGROUND

The skin is the human body's largest organ, colonized by a diverse range of microorganisms, the majority of which are harmless or even beneficial to their host. These microorganisms often provide vital functions that the human genome has not yet evolved to perform. In this way, the skin constantly regulates a balance between host-human and microorganism. Disruptions in this delicate balance, on either side, can result in serious skin disorders or infections.

Pathogens on the skin are known to cause illness and may be easily transmitted from one person to another. Some pathogens stick strongly to skin. Typically, when pathogens stick to skin, they are more difficult to remove or kill using traditional approaches to skin cleaning and disinfection such as washing with soap or using a waterless sanitizer. Pathogens that are stuck to skin are more dangerous because they remain on the skin longer. The longer the pathogen is on the skin, the more the chance that they will either cause infections on the person with them or be shared with other people.

There is an increasing interest in finding alternative ways to control pathogens without the use of more antimicrobials. Probiotics are being used to control microbes on skin in new ways that do not require the use of antimicrobials. Probiotics are live or inactivated microorganisms that, when either present as part of the normal microbiota or when administered in adequate amounts, confer a health or cosmetic benefit on the host. Benefits from probiotics can be from the microbial components directly or can come from the byproducts of bacterial growth.

It is known that some pathogens and beneficial normal (probiotic) skin microbes compete with each other for binding sites on skin. U.S. Patent Publication No. 2008/0261916 (the '916 Publication) describes a mixture of prebiotic ingredients used for the prevention, alleviation or treatment of diseases or disorders and that can be administered topically or orally. However, the '916 Publication does not decrease the adherence of pathogens on skin or reducing pathogen levels on skin and does not help prevent skin infections, skin-to-skin germ transmission, skin-to-inanimate object transmission, human-to-animal-to-human transmission, or human-to-food-to-human transmission.

Antimicrobial peptides (AMPs) comprise a wide range of natural and synthetic peptides that are made of oligopeptides containing a varying number of amino acids. AMPs may be produced by a host, or by the skin microbiota itself. AMPs are essential components of host defense against infections present in all domains of life. AMPs are produced by all complex organisms and have diverse and intricate antimicrobial activities. As a whole, these peptides demonstrate a broad range of antiviral and antibacterial activities through an array of modes of action. AMPs have been found to kill Gram-negative and Gram-positive bacteria, certain viruses, parasites and fungi. Some research suggests that they can also enhance the internal immunity of complex organisms against a broad range of bacteria and viruses. In addition to the innate immune system present in all animals, vertebrates evolved an adaptive immune system based on specific recognition of antigens. Increasing evidence suggests that AMPs released in response to an invasion of microbial can activate adaptive immunity by attracting antigen-presenting dendritic cells to the invasion site.

Therefore, it would be beneficial to design a new sanitizing composition that is safe for topical use, restores the natural balance of bacteria on the skin, including decreasing the adherence of pathogens on the skin, and can also increase the production and/or activity of antimicrobial peptides.

SUMMARY

According to some exemplary embodiments, a sanitizing composition for restoring skin's natural balance of bacteria is provided. The sanitizing composition includes about 0.005 wt. % to 15.0 wt. % of an active ingredient that is one or more of a probiotic, a probiotic derivative, and a prebiotic. The sanitizing composition also includes one or more ingredients that deliver a sanitizing effect. Application of the sanitizing composition reduces pathogen binding on the surface of the skin by an amount that is statistically significant compared to an otherwise identical sanitizing composition without the active ingredient.

In some exemplary embodiments, the one or more ingredients that deliver a sanitizing effect is an anti-microbial agent that can be one or more of an alcohol and a quaternary ammonium compound. The alcohol can be one or more $C_{1-8}$ alcohols, such as methanol, ethanol, propanol, pentanol, hexanol, and isomers and mixtures thereof. In some exemplary embodiments, the alcohol is included in an amount above about 70 wt. %, based on the total weight of the sanitizing composition.

In some exemplary embodiments, the active ingredient is a probiotic or probiotic derived ingredient, which can be selected from a strain of one or more the following: *Lactobacillus*, strains and derivatives of *Clostridia*, strains and derivatives of *Bifidobacterium*, strains and derivatives of *Saccharomyces*, strains and derivatives of *Lactococcus*, strains and derivatives of *Pedicoccus*, strains and derivatives of *Enterococcus*, strains and derivatives of *Escherichia*, strains and derivatives of *Alcaligenes*, strains and derivatives of *Corynebacterium*, strains and derivatives of *Bacillus*, and strains and derivatives of *Propionibacterium*. In some exemplary embodiments, the probiotic or probiotic derived ingredient is a *Bacillus* ferment.

In some exemplary embodiments, the sanitizing composition comprises from about 0.05 to about 5.0 wt. % or from about 0.1 to about 1.0 wt. % of the active ingredient, based on the total weight of the sanitizing composition.

In some exemplary embodiments, the sanitizing composition further comprises one or more skin conditioning agents.

In some exemplary embodiments, the sanitizing composition contains up to about 20.0 wt. % of a humectant as the skin conditioning agent, selected from the group consisting of propylene glycol, hexylene glycol, 1,4-dihydroxyhexane, 1,2,6-hexanetriol, sorbitol, butylene glycol, caprylyl glycol, propanediols, such as methyl propane diol, dipropylene glycol, triethylene glycol, glycerin (glycerol), polyethylene glycols, ethoxydiglycol, polyethylene sorbitol, glyceryl caprylate/caprate, and combinations thereof.

In some exemplary embodiments, the sanitizing composition also contains up to about 20.0 wt. % of one or more plug preventing additives, based on the total weight of the sanitizing composition.

In some exemplary embodiments, the sanitizing composition also contains up to about 10.0 wt. % of a moisturizing ester, selected from the group consisting of selected from the group consisting of cetyl myristate, cetyl myristoleate, and other cetyl esters, diisopropyl sebacate, isopropyl myristate, and combinations thereof.

In some exemplary embodiments, the sanitizing composition further comprises a carrier, which can be water.

In another exemplary embodiment, a skin treatment method for reducing pathogen binding on skin is provided. The method includes applying a sanitizing composition to a skin surface, wherein the sanitizing composition includes about 0.005 wt. % to about 15.0 wt. % of an active ingredient. The active ingredient may be one or more of a probiotic, a probiotic derivative, or a prebiotic. The sanitizing composition also includes one or more ingredients that deliver a sanitizing effect. Application of the sanitizing composition reduces pathogen binding on skin by a statistically significant amount, as compared to an otherwise identical sanitizing composition without the active ingredient.

In other exemplary embodiments, a sanitizing composition for increasing the production and/or activity of antimicrobial peptides is provided. The sanitizing composition includes about 0.005 wt. % to about 15.0 wt. % of an active ingredient that is one or more of a probiotic, a probiotic derivative, or prebiotic. The sanitizing composition also includes one or more ingredients that deliver a sanitizing effect. Application of the sanitizing composition increases the production and/or activity of antimicrobial peptides by an amount that is statistically significant compared to an otherwise identical sanitizing composition without the active ingredient.

In some exemplary embodiments, the sanitizing composition increases the production and/or activity of defensins by at least about 44% and the production and/or activity of cadherins by at least 75%, both relative to an otherwise identical sanitizing composition without the active ingredient.

In another exemplary embodiment, a skin treatment sanitizing composition is provided. The sanitizing composition comprises about 0.005 wt. % to 15.0 wt. % of an active ingredient comprising one or more of a probiotic, a probiotic derivative, and a prebiotic, about 40.0 wt. % to about 95 wt. % of one or more ingredients that deliver a sanitizing effect, about 0.01 wt. % to about 10.0 wt. % of one or more skin conditioners, and about 0.01 wt. % to about 5.0 wt. % of a viscosity modifier.

In some exemplary embodiments, a sanitizing composition for restoring skin's natural balance of bacteria is provided. "Restoring skin's natural balance" means helping to change the ratio of transient pathogens to resident microbes (i.e., restores the "good" bacteria and reduces the amount of transient pathogens) The sanitizing composition comprises about 0.005 wt. % to 15.0 wt. % of an active ingredient comprising one or more of a probiotic, a probiotic derivative, or prebiotic, about 40.0 wt. % to about 95.0 wt. % of one or more ingredients that deliver a sanitizing effect, about 0.01 wt. % to about 5.0 wt. % of a foaming agent, and about 0.01 wt. % to about 10.0 wt. % of one or more skin conditioners.

In some exemplary embodiments, a sanitizing composition for reducing skin irritation is provided. The sanitizing composition includes about 0.005 wt. % to 15.0 wt. % of an active ingredient that is one or more of a probiotic, a probiotic derivative, and a prebiotic. The sanitizing composition also includes about 40.0 wt. % to 95.0 wt. % of one or more ingredients that deliver a sanitizing effect. Application of the sanitizing composition decreases pro-inflammatory mark production and/or activity by an amount that is statistically significant compared to an otherwise identical sanitizing composition without the active ingredient.

In some exemplary embodiments, the sanitizing composition decreases the production and/or activity of pro-inflammatory markers, such as interleukins, by at least about 30%, relative to an otherwise identical sanitizing composition without the active ingredient.

According to some exemplary embodiments, a nasal spray sanitizing composition is provided. The nasal spray comprises one or more $C_{1-8}$ alcohols and about 0.005 wt. % to about 15.0 wt. % of an active ingredient that is one or more of a probiotic, a probiotic derivative, and a prebiotic. Application of the nasal spray reduces pathogen binding in the nose by an amount that is statistically significant compared to an otherwise identical nasal spray without the active ingredient.

In some exemplary embodiments, the nasal spray further comprises one or more fragrances. In some exemplary embodiments, the active ingredient comprises a topical probiotic and is essentially free of oral probiotics.

DETAILED DESCRIPTION

Figure 1:
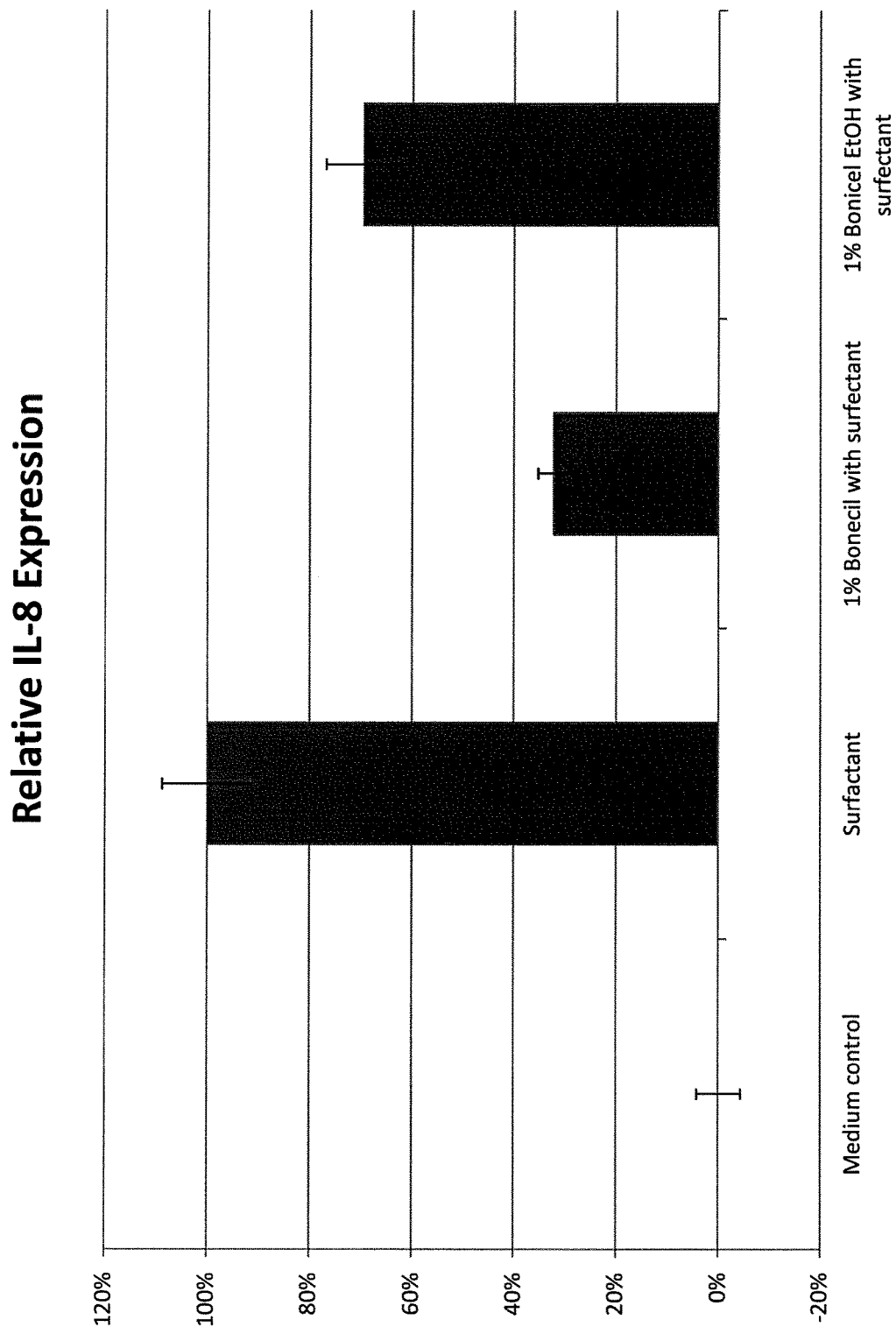
FIG. 1 illustrates an exemplary graph of the relative Interleukin 8 expression in sanitizing compositions containing 1.0 wt. % Bonicel™ compared to a control.

Unless otherwise defined, all technical and scientific terms used herein have the same meaning as commonly understood by one of ordinary skill in the art to which this application pertains. Although other methods and materials similar or equivalent to those described herein may be used in the practice or testing of the exemplary embodiments, exemplary suitable methods and materials are described below. In case of conflict, the present specification including definitions will control. In addition, the materials, methods, and examples are illustrative only and not intended to be limiting of the general inventive concepts.

The terminology as set forth herein is for description of the exemplary embodiments only and should not be construed as limiting the application as a whole. Unless otherwise specified, "a," "an," "the," and "at least one" are used interchangeably. Furthermore, as used in the description of the application and the appended claims, the singular forms "a," "an," and "the" are inclusive of their plural forms, unless contradicted by the context surrounding such.

The term "microorganism" or "microbe" as used herein, refers to a tiny organism, such as a virus, protozoan, fungus, or bacterium that can only be seen under a microscope. The collection of microorganisms that live in an environment makes up a microbiota. For example human skin microbiota is all of the microbes on skin or a hospital microbiota would include all of the microbes in a hospital building. The term microbiome is used when referring to the entire habitat, including the microbiota as well as their genomes and the surrounding environment of the microbiota.

The phrase "statistically significant" means p<0.05 for a test composition vs. a control that does not contain the active ingredient. The analysis is completed using 1) a T-test (a statistical examination of two population means) when only comparing one test article vs. one control); or 2) an analysis of variance (ANOVA) test when comparing two or more test articles vs. controls.

The general inventive concepts relate to a sanitizing composition that contains an active ingredient that includes one or more of a probiotic, a probiotic-derived ingredient, and a prebiotic and/or prebiotic-derived ingredient. Generally, the active ingredient helps to restore skin's natural balance of bacteria and increase the production and/or activity of antimicrobial peptides. In some exemplary embodiments, the sanitizing composition disclosed herein prevents pathogens from adhering to a surface, such as human skin or any inanimate surface. Such adherence prevention includes not only impeding the binding of a pathogen, but also promoting detachment of any already bound pathogen, and otherwise limiting the presence of such pathogens on a surface.

In some exemplary embodiments, the sanitizing composition comprises one or more probiotics and/or probiotic-derived ingredients (probiotic derivatives). In general, the probiotic can be any living or dead microorganism that provides a health benefit to the host. The probiotic derivative can be any derivative of any type of probiotic. In some exemplary embodiments, the derivative is one or more of an excretion from a probiotic and a fragment of a probiotic. The fragment can be any portion of the probiotic microorganism including any portion of its DNA thereof.

Some non-limiting examples of probiotic and probiotic-derived ingredients include strains and derivates of the following families: Actinomycetaceae, Corynebacteriaceae, Nocardiaceae, Intrasporangiaceae, Micrococcaceae, Propionibacteriacea, Bacteroidaceae, Porphyromonadaceae, Flavobacteriaceae, Sphingobacteriaceae, Bacillaceae, Exiguobacteraceae, Gemellaceae, Planococcaceae, Staphlococcaceae, Carnobacteriaceae, Aeorcoccaceae, Lactobacillaceae, Acidaminacoccaceae, Clostridiaceae, Lachnospiraceae, Peptostreptococcaceae, Veillonellaceae, Caulobactereaceae, Acetobacteraceae, Rhodobacteriaceae, Bradyrhizobiaceae, Brucellaceae, Sphingomonadaceae, Comamonadaceae, Neisseriaceae, Enterobaceriaceae, Pseudomonodaceae, Moraxellaceae, Pasteurellaceae, Xanthomonadaceae, Fusobacteriaceae, Chloroflexi, Chloroplasts, Cyanobacteria, and Streptophyta, for example. In some exemplary embodiments, the active ingredient is a probiotic or probiotic derived ingredient, which can be selected from a strain of one or more the following: *Lactobacillus*, strains and derivatives of *Clostridia*, strains and derivatives of *Bifidobacterium*, strains and derivatives of *Saccharomyces*, strains and derivatives of *Lactococcus*, strains and derivatives of *Pedicoccus*, strains and derivatives of *Enterococcus*, strains and derivatives of *Escherichia*, strains and derivatives of *Alcaligenes*, strains and derivatives of *Corynebacterium*, strains and derivatives of *Bacillus*, and strains and derivatives of *Propionibacterium*.

In some exemplary embodiments, the probiotic or probiotic derived ingredient is a ferment of *Bacillus coagulans*. *Bacillus* is a genus of Gram-positive, rod-shaped bacteria of the phylum Fimicutes. *Bacillus* can be either aerobic or, under certain conditions, anaerobic and produces endospores. *Bacillus* exhibits a wide range of physiologic properties that allows it to thrive in a number of different habitats—most *Bacillus* strains are resistant to heat, cold, radiation, and disinfectants. A *Bacillus* ferment is sold under the trade name Bonicel™ by Ganeden Biotech, Inc. in Cleveland, Ohio and is the supernatant produced by *Bacillus coagulans* GBI-30, 6086 (collectively referred to herein as "Bonicel™"). Bonicel™ is produced though a fermentation process which ensures the formulation includes the maximum amounts of enzymes, bateriocins, and L+ Lactic acid. Additional probiotic or probiotic derived ingredients may include Repair Complex CLR™, EcoSkin® from Solabia Group, Leucidal® Liquid SF from Active Micro Technologies, ProSynergen™ from Lonza Group, ProBioBalance CLR™ from CLR, Yogurtene® Balance from Lonza Group, Biodynes™ from Lonza Group, and *Bifidobacterium Longum* Lysate.

In some exemplary embodiments, the active ingredient is one or more prebiotics and/or prebiotic derived ingredients (prebiotic derivatives). Generally, the prebiotic can be any compound that affects the ecology and/or environment of the microbiome by increasing good bacteria and/or decreasing bad bacteria. Non-limiting examples of ways that the prebiotic can affect the ecology and/or environment of the microbiome include, for example, feeding particular organisms, by altering oxygen levels, by changing temperature, by altering water content, by changing salinity, and/or by altering nutrient levels/types. Some non-limiting examples of prebiotic ingredients include alpha and beta-glucan oligosaccharides, trans-galactooligosaccharides, xylooligosaccharide, frutooligosaccharides, lactulose, *ginseng*, black current extract, sugar-beet extract, garlic extract, bark extract, chicory extract, corn extract, nerolidol extract, xylitol, and pectin. Additional prebiotic ingredients may include EmulGold™ Fibre by Kerry Ingredients, Genu® Explorer Pectin by CP Kelco, Orafti® from Beneo, VitaFiber™ from BioNeutra, Konjac Glucomannan Hydrolysates, and Oat Beta Glucan from VegeTech.

In some exemplary embodiments, the sanitizing composition comprises a mixture of probiotics/probiotic derivatives and prebiotics/prebiotic derivatives as the active ingredient.

In some embodiments, the active ingredient functions to simulate the production and/or activity of antimicrobial peptides and thereby increase the overall concentration of AMPs on the surface of the skin. In some exemplary embodiments, the sanitizing composition disclosed herein includes an effective amount of active ingredient to increase the production and/or activity of at least one antimicrobial peptide on, for example, the skin. The sanitizing composition can increase the production and/or activity of a wide variety of antimicrobial peptides, such as, for example defensins and cathelicidin-related AMPs and decrease proinflammatory factors. Such increased production and/or activity helps the skin's ability to defend against germs and helps improve the skin's innate immunity. While sanitizing compositions that can increase the skin's innate immunity or the production and/or activity on the skin are often discussed herein, it is to be appreciated that the sanitizing compositions can provide the same benefits to nails, epithelial cells, as well as other parts of mammalian bodies.

The skin naturally produces AMPs, but the levels produced are not sufficient to produce the desired effect of long lasting germ defense and innate immunity on the skin. The active ingredient of the exemplary embodiments described herein has been found to help increase the production and/or activity of AMPs at levels significantly higher than the skin alone.

In one exemplary embodiment, the sanitizing composition increases the production and/or activity of defensins. Defensins are cationic proteins that function as host defense peptides and have been found in vertebrates, invertebrates, and some plants. Defensins include at least α-defensins, β-defensins, and θ-defensins. In some exemplary embodiments, the sanitizing composition increases the production and/or activity of β-defensins, such as HBD-2.

In some exemplary embodiments, the sanitizing composition increases the production and/or activity of cathelicidin-related antimicrobial peptides. Cathelicidins play a vital role in mammalian innate immunity against invasive bacterial infections. In some exemplary embodiments, the sanitizing composition increases the production and/or activity of the cathelcidin-related AMP, LL-37.

In other exemplary embodiments, the sanitizing composition decreases the production and/or activity of pro-inflammatory factors. One such pro-inflammatory factor is cytokines, which are a group of small proteins that are involved in cell signaling. There are numerous groups of cytokines including chemokiens, interferons, interleukins, lymphokines, and tumor necrosis factors. Interleukins are one group of cytokines and include 17 different families, interleukins 1-17. In some exemplary embodiments, the sanitizing composition increases the production and/or activity of the pro-inflammatory factor, cytokines. In some exemplary embodiments, the sanitizing composition increases the production and/or activity of the cytokine, interleukins, such as interleukin-8 (IL-8).

In some exemplary embodiments, the sanitizing composition increases the production and/or activity of cadherins. In some exemplary embodiments, the cadherins can be within the desmosomal class and within the desmocollin subclass of cadherins. Cadherins are type-1 trasmembrane proteins that are involved in cell adhesion, specifically adhesions junctions in binding cells one another. In this way, they are referred to herein as skin junction biomarkers. In some exemplary embodiments, the sanitizing composition increases the production and/or activity of the skin junction biomarker, desmosomals, such as desmocollin-3 (DCS3).

Traditionally, it has been found that compositions used to stimulate the production and/or activity of AMPs also cause skin inflammation and/or skin irritation. However, it has been discovered that a sanitizing composition comprising the subject active ingredient is capable of increasing the production and/or activity of at least one AMP on the skin without causing irritation/inflammation of the skin.

In some embodiments, the active ingredient helps to restore the microbial balance of bacteria on the skin. A human's skin microbiota includes resident skin microorganisms that are continuously present on the skin. The resident skin microorganisms are usually non-pathogenic and either commensals (not harmful to their host) or mutualistic (offer a benefit). Resident skin microorganisms are adapted to survive on skin and they eat, reproduce, and excrete, which has an effect on the skin. However, certain transient skin microorganisms may attempt to colonize the skin, which could upset a healthy microbiome. Such transient skin microorganisms may include pathogens, such as pathogenic bacteria, yeasts, viruses, and molds. The particular make-up of a human's microbiome may be different than the make-up of another human's. A resident skin microorganism on one person may be a transient on another.

While the skin naturally works to regulate the microbiota on the surface, the active ingredients disclosed herein have been found to help in regulating and restoring this natural balance.

In some exemplary embodiments, the sanitizing composition comprises up to about 15.0 weight percent (wt. %) of the active ingredient, or up to about 8.0 wt. %, or up to about 5.0 wt. %, or up to about 3.0 wt. %, or up to about 2.0 wt. % of the active ingredient, based on the total weight of the sanitizing composition. The sanitizing composition may comprise at least about 0.001 wt. % of the active ingredient, or at least about 0.005 wt. %, or at least about 0.01 wt. %, or at least about 0.05 wt. %, or at least about 0.1 wt. %, or at least about 0.5 wt. %, or at least about 1.0 wt. % of the active ingredient, based on the total weight of the sanitizing composition.

In some exemplary embodiments, the effective amount of active ingredient comprises from about 0.005 to about 15.0 wt. %, or from about 0.02 to about 5.0 wt. %, or from about 0.5 to about 2.0 wt. %, based on the total weight of the sanitizing composition. In other exemplary embodiments, the effective amount of active ingredient comprises about 0.1 to about 1.0 wt. %, based on the total weight of the sanitizing composition. In one exemplary embodiment, the sanitizing composition comprises about 0.08 to about 0.2 wt. % of the active ingredient, based on the total weight of the sanitizing composition.

In some exemplary embodiments, the sanitizing composition is a sanitizing composition used for application to surfaces, such as the human skin. In some other exemplary embodiments, the sanitizing composition is used for application in various human orifices, such as the nose. While surfaces on the human body, such as the skin or nose are discussed herein, it is to be appreciated that the compositions and methods disclosed herein can be used on non-mammalian and inanimate objects and surfaces.

The sanitizing composition may be in the form of a gel, a foam, a salve, a wipe, a cream, etc. A wide variety of vehicles may be used to deliver the sanitizing composition, such as, for example pads, bandages, patches, sticks, aerosol dispersers, pump sprays, trigger sprays, canisters, foam pumps, wipes, and the like. The sanitizing composition may be applied to the skin before, during, or after skin cleaning. In some exemplary embodiments, the sanitizing composition is applied after skin cleaning.

In some exemplary embodiments, the sanitizing composition comprises one or more ingredients that have a sanitizing effect. The term "ingredient with a sanitizing effect" is meant to include any compound, ingredient, molecule, or combination or blend thereof that achieves at least a 2-log reduction in the number of viable microorganisms in vitro after 60 seconds according to the ASTM E2783 11(2016) time kill test method. The ingredient with a sanitizing effect can be an anti-microbial agent. Anti-microbial agents are compounds that kill and/or protect against the growth of microorganisms.

In some exemplary embodiments, the ingredient with a sanitizing effect is one or more of alcohol, povidone-iodine, triclosan, triclocarban, chlorohexidine, chlorine, hexachlorophene, iodine, chloroxyenol, chlorine dioxide, oxidizing agents, polyhexamethylene biguanide (PHMB), hydrogen peroxide, phenoxyethanol, iodine, antimicrobial peptides, hypochlorites, lysozymes, alkyl gallates, quinones, catechins, urea, biguanide, oxygen, and quaternary ammonium compounds such as benzalkonium chloride or benzethonium chloride. In some exemplary embodiments, the ingredient with a sanitizing effect is an aldehyde donor, such as a formaldehyde donor. In some exemplary embodiments the ingredient with a sanitzing effect is a surfactant. In some exemplary embodiments, the surfactant is an anionic surfactant, a cationic surfactant, or a nonionic surfactant.

In some exemplary embodiments, the ingredient with a sanitizing effect is an acid. In some exemplary embodiments, the acid is an organic acid. In some exemplary embodiments, the acid is one or more of citric acid, lactic acid, hypochlorous acid, caffeic acid, and the like. In some exemplary embodiments, the acid is a peracid, such as peracitic acid, perlactic acid, peroctanoic acid, perbenzoic acid, peracetic acid, perpropionic acid, performic acid, and the like. The peracid can be an inorganic or organic peracid. In some exemplary embodiments, the ingredient with a sanitizing effect is an essential oil and/or derivative thereof. Non-limiting examples of such compounds include carvacrol, thymol, linalool, farnesol, and the like. In some exemplary embodiments, the ingredient with a sanitizing effect is a carboxylic acid, such as a mono-, di-, tri-, or tetra-carboxylic acid or a polymeric carboxylic acid.

In some exemplary embodiments, the ingredient with a sanitizing effect is a compound that contains one or more of silver and copper or alloys thereof (such as brasses, bronzes, cupronickel, and the like). In some exemplary embodiments, the silver or copper has been ionized. In some exemplary embodiments, the ingredient with a sanitizing effect is elemental copper or elemental silver. In some exemplary embodiments, the ingredient with a sanitizing effect is a silver salt or copper salt. In some other exemplary embodiments, the ingredient with a sanitizing effect is a titanium dioxide based solution.

In some exemplary embodiments, the ingredient with a sanitizing effect is an organic peroxide, a phenolic compound, a free radical, or a glycol. In some exemplary embodiments, the ingredient with a sanitizing effect is an ion, such as a hydroxyl ion or a metal ion. In some exemplary embodiments, the ingredient with a sanitizing effect is any compound that has been identified or approved by the United States Food and Drug Administration as being suitable as an active ingredient/anti-microbial agent in a sanitizing composition.

In some exemplary embodiments, the ingredient that has a sanitizing effect in the sanitizing composition is an alcohol or combination of alcohols. By alcohol, it is meant any organic compound which has a hydroxyl functional group bonded to a saturated carbon atom. Alcohol has antimicrobial properties and has the ability to kill many forms of bacteria, fungi, and viruses. In some embodiments, the alcohol is a $C_{1-8}$ alcohol, i.e. an alcohol containing 1 to 8 carbon atoms. Such alcohols may be referred to as lower alkanols. Examples of lower alkanols include, but are not limited to, methanol, ethanol, propanol, butanol, pentanol, hexanol, and isomers or mixtures thereof. The alcohol may be either pure alcohol or denatured alcohol. In one or more exemplary embodiments, the alcohol comprises ethanol, propanol, or butanol, or isomers or mixtures thereof. In one or more exemplary embodiments, the alcohol comprises isopropanol. In other exemplary embodiments, the alcohol comprises ethanol. In one or more exemplary embodiments, the sanitizing composition comprises a mixture of alcohols. In one or more exemplary embodiments, the sanitizing composition comprises a mixture of ethanol and isopropanol. In one or more exemplary embodiments, the sanitizing composition comprises a mixture of isopropanol and n-propanol. In one exemplary embodiment, the sanitizing composition comprises ethanol.

While $C_{1-8}$ alcohols are discussed herein as able to deliver the necessary sanitizing effect, it is envisioned that longer alcohols (alcohols with more than 8 carbon atoms), or alcohols with various other functional groups would be similarly suitable. For example, in addition to the hydroxyl functional group, the alcohol may further contain esters, carboxylic acids, ethers, amides, amines, alkyl halides, phenyls, as well as other carbonyl-containing functional groups. The alcohol can also be an aliphatic alcohol or an aromatic alcohol.

In some exemplary embodiments, the sanitizing composition comprises at least about 1.0 wt. % $C_{1-8}$ alcohol, based on the total weight of the sanitizing composition. In one embodiment, the sanitizing composition comprises at least about 2.0 wt. % $C_{1-8}$ alcohol, in another embodiment, the sanitizing composition comprises at least about 10.0 wt. % $C_{1-8}$ alcohol, in another embodiment, the sanitizing composition comprises at least about 20.0 wt. % $C_{1-8}$ alcohol, in another embodiment, the sanitizing composition comprises at least about 40.0 wt. % $C_{1-8}$ alcohol, in another embodiment, the sanitizing composition comprises at least about 50.0 wt. % $C_{1-8}$ alcohol, in another embodiment, the sanitizing composition comprises at least about 60.0 wt. % $C_{1-8}$ alcohol, in another embodiment, the sanitizing composition comprises at least about 65.0 wt. % $C_{1-8}$ alcohol, in yet another embodiment, the sanitizing composition comprises at least about 70.0 wt. % $C_{1-8}$ alcohol, and in still yet another embodiment, the sanitizing composition comprises at least about 80.0 wt. % $C_{1-8}$ alcohol, based on the total weight of the sanitizing composition. In other embodiments, the sanitizing composition comprises from about 60.0 to about 95.0 wt. % $C_{1-8}$ alcohol, based on the total weight of the sanitizing composition. In other exemplary embodiments, the sanitizing composition comprises from about 73.0 to about 78.0 wt. % $C_{1-8}$ alcohol, based on the total weight of the sanitizing composition. More or less alcohol may be required in certain instances, depending particularly on other ingredients and/or the amounts thereof employed in the sanitizing composition.

The ability to use the active ingredients of the exemplary embodiments described herein in the presence of alcohol was particularly surprising. Typically, the presence of alcohol is thought to kill or disrupt bacteria (such as *Bacillus coagulans* in Bonicel™). The exact mode thereof is not clear, however the following probable effects have been offered: (1) alcohol affects and at high concentrations actually disrupts the lipid cell membrane changing mobility therein, (2) alcohol traverses the cell membrane and denatures proteins, and (3) alcohol acts as a solvent, changing the environment in which enzymes catalyze reactions. However, surprisingly, the present composition including high concentrations of alcohol and a probiotic, probiotic-derived or prebiotic active ingredient was prepared without observing these traditional adverse reactions between the alcohol and bacteria. In fact, in some exemplary embodiments, the prebiotic, probiotic, or probiotic-derived ingredient has enhanced effectiveness as compared to performance in non-alcohol systems.

In other exemplary embodiments, where the ingredient with a sanitizing effect is not alcohol, the amount of the ingredient is not particularly limited. In some exemplary embodiment, the ingredient with a sanitizing effect can be added in an amount up to about 95.0 wt. %, or about 85.0 wt. %, or about 75.0 wt. %, or about 65.0 wt. %, based on the total weight of the sanitizing composition. In other exemplary embodiments, the ingredient with a sanitizing effect can be added in an amount as low as about 0.001 wt. %, or about 0.01 wt. %, or about 0.1 wt. %. In some exemplary embodiments, the ingredient with a sanitizing effect can be added in an amount from about 0.01 to about 15.0 wt. %, based on the total weight of the sanitizing composition. In some exemplary embodiments, the ingredient with a sanitizing effect is added in an amount from about 0.5 to about 7.5 wt. %, or about 0.75 to about 5.0 wt. %, or from about 1.0 to about 4.0 wt. %, based on the total weight of the sanitizing composition.

In some exemplary embodiments, the sanitizing composition comprises a carrier. The carrier can be any suitable compound able to effectively deliver and/or transport the sanitizing composition. In some exemplary embodiments, the carrier is water or a base cleaner. In other exemplary embodiments, the sanitizing composition does not include any carrier and is delivered as a concentrate.

In some exemplary embodiments, the sanitizing composition includes water as the carrier in an amount *quantum sufficit* (q.s.). In some exemplary embodiments, the sanitizing composition comprises at least about 1.0 wt. % water, in another embodiment the sanitizing composition comprises at least about 10.0 wt. % water, in another embodiment, the sanitizing composition comprises at least about 20.0 wt. % water, in another embodiment, the sanitizing composition comprises at least about 30.0 wt. % water, in another embodiment, the sanitizing composition comprises at least about 40.0 wt. % water, in another embodiment, the sanitizing composition comprises at least about 50.0 wt. % water, and in yet another embodiment, the sanitizing composition comprises at least about 60.0 wt. % water, and in still yet another embodiment, the sanitizing composition comprises at least about 70.0 wt. % water, based on the total weight of the sanitizing composition. In other embodiments, the sanitizing composition comprises from about 20.0 wt. % to about 30.0 wt. % water, based on the total weight of the sanitizing composition. In one exemplary embodiment, the sanitizing composition comprises from about 20.0 to about 24.0 wt. % water, based on the total weight of the sanitizing composition. More or less water may be required in certain instances, depending particularly on other ingredients and/or the amounts thereof employed in the sanitizing composition.

In one or more exemplary embodiments, the sanitizing composition includes one or more skin-conditioners. Various classes or types of skin-conditioners can be used such as humectants, emollients, and other miscellaneous compounds which exhibit occlusive properties upon application to the skin. Non-limiting examples of suitable skin conditioners and emollients include aloe, vitamin E, vitamin E acetate (tocopheryl acetate), Vitamin $B_3$ (niacinamide), $C_{6-10}$ alkane diols, sodium salt of pyroglutamic acid (sodium PCA), PEG-7 glyceryl cocoate, coco-glucoside and/or glyceryl oleate (Lamisoft® PO), and polyquaternium, such as polyquaternium 10 and 39.

In some exemplary embodiments, if an emollient or one of the miscellaneous skin-conditioners is included, such compound can be included in the sanitizing composition in an amount from about 0.0001 to about 10.0 wt. %, in other embodiments, from about 0.0005 to about 5.0 wt. %, based on the total weight of the sanitizing composition. In one exemplary embodiment, the miscellaneous skin conditioner is present in an amount from about 0.1 to about 2.0 wt. %, based on the total weight of the sanitizing composition, and in yet another exemplary embodiment, from about 0.5 to about 1.0 wt. %, based on the total weight of the sanitizing composition.

In some exemplary embodiments, the sanitizing composition includes one or more humectants as the skin conditioner. Non-limiting examples of humectants include propylene glycol, hexylene glycol, 1,4-dihydroxyhexane, 1,2,6-hexanetriol, sorbitol, butylene glycol, caprylyl glycol, propanediols, such as methyl propane diol, dipropylene glycol, triethylene glycol, glycerin (glycerol), polyethylene glycols, ethoxydiglycol, polyethylene sorbitol, and combinations thereof. Other humectants include glycolic acid, glycolate salts, lactate salts, urea, hydroxyethyl urea, alpha-hydroxy acids, such as lactic acid, sodium pyrrolidone carboxylic acid, hyaluronic acid, chitin, glyceryl caprylate/caprate (GCC), and the like. In one exemplary embodiment, the humectant is a mixture of caprylyl glycol and glycerin.

Examples of polyethylene glycol humectants include PEG-4, PEG-6, PEG-7, PEG-8, PEG-9, PEG-10, PEG-12, PEG-14, PEG-16, PEG-18, PEG-20, PEG-32, PEG-33, PEG-40, PEG-45, PEG-55, PEG-60, PEG-75, PEG-80, PEG-90, PEG-100, PEG-135, PEG-150, PEG-180, PEG-200, PEG-220, PEG-240, and PEG-800.

In some exemplary embodiments, the humectant is included in the sanitizing composition in an amount up to about 20.0 wt. %, or up to about 15.0 wt. %, or up to about 12.0 wt. %, or up to about 10.0 wt. %, or up to about 8.0 wt. % or up to about 8.0 wt. %, or up to about 3.0 wt. %, based on the total weight of the sanitizing composition. In some exemplary embodiments, the humectant is included in an amount from about 0.001 wt. %, or from about 0.01 wt. %, or from about 0.05 wt. %, or from about 0.1 wt. %, or from about 0.5 wt. %, or from about 0.7 wt. %, or from about 1.0 wt. %, or from about 1.5 wt. %, or from about 2.0 wt. %, based on the total weight of the sanitizing composition. In one exemplary embodiment, the humectant is included in an amount from about 0.4 to about 3.0 wt. %, based on the total weight of the sanitizing composition. In some exemplary embodiments, the humectant is included in an amount from about 0.005 to about 10.0 wt. %, or from about 0.01 to about 5.0 wt. %, based on the total weight of the sanitizing composition. In one exemplary embodiment the humectant is included in an amount from about 0.1 to about 4.0 wt. %, based on the total weight of the sanitizing composition.

In some exemplary embodiments, the sanitizing composition further comprises a plug-preventing additive. In general, the additive prevents the hydroalcoholic gel from coagulating into solid or semi-solid material that may deposit onto a surface or plug a dispenser nozzle. In some exemplary embodiments, the plug-preventing additive can also, as discussed above, act as the humectant.

In one exemplary embodiments, the plug-preventing additive comprises a hydrocarbon chain with two or more carbon atoms. The hydrocarbon can be branched or straight and can also be cyclic or linear. The hydrocarbon can have any number of various functional groups including, but not limited to, amines, esters, carboxylic acids, ethers, amides, alkyl halides, alcohols, phenyls, as well as other carbonyl-containing functional groups. The hydrocarbon molecule can be anionic, cationic, or non-ionic.

In one exemplary embodiment, the hydrocarbon contains one or more esters. In some exemplary embodiments, the plug-preventing additive comprises a monomeric or polymeric di-ester, tri-ester, tetra-ester, penta-ester, or hexa-ester, or a polymeric monoester. In one or more embodiments, the plug-preventing additive includes one or more of $C_1$-$C_{30}$ alcohol esters of $C_1$-$C_{30}$ carboxylic acids, ethylene glycol monoesters of $C_1$-$C_{30}$ carboxylic acids, ethylene glycol diesters of $C_1$-$C_{30}$ carboxylic acids, propylene glycol monoesters of $C_1$-$C_{30}$ carboxylic acids, propylene glycol diesters of $C_1$-$C_{30}$ carboxylic acids, $C_1$-$C_{30}$ carboxylic acid monoesters and polyesters of polypropylene glycols, $C_1$-$C_{30}$ carboxylic acid monoesters and polyesters of polypropylene glycols, $C_1$-$C_{30}$ carboxylic acid monoesters and polyesters of $C_4$-$C_{20}$ alkyl ethers, $C_1$-$C_{30}$ carboxylic acid monoesters and polyesters of di-$C_8$-$C_{30}$ alkyl ethers, and mixtures thereof.

Non-limiting examples of plug-preventing additives with esters include acetyl tributyl citrate, acetyl triethyl citrate, acetyl triethylhexyl citrate, acetyl trihexyl citrate, butyl benzyl phthalate, butyl phthalyl butyl glycolate, butyroyl trihexyl citrate, dibutyl adipate, dibutyloctyl malate, dibutyl oxalate, dibutyl phthalate, dibutyl sebacate, dicapryl adipate, dicaprylyl/capryl sebacate, diethylene glycol dibenzoate, diethylene glycol diethylhexanoate/diisononanoate, diethylene glycol diisononanoate, diethylene glycol rosinate, diethylhexyl adipate, diethylhexyl phthalate, diethylhexyl sebacate, diethylhexyl succinate, diethylhexyl terephthalate, diethyl oxalate, diethyl phthalate, diethyl sebacate, diethyl succinate, diisoamyl malate, diisobutyl adipate, diisobutyl maleate, diisobutyl oxalate, diisocetyl adipate, diisocetyl dodecanedioate, diisodecyl adipate, diisononyl adipate, diisocetyl adipate, diisooctyl maleate, diisooctyl sebacate, diisopropyl adipate, diisopropyl oxalate, diisopropyl sebacate, diisopropyl dimer dilinoleate, diisostearyl adipate, diisostearyl fumarate, diisostearyl glutarate, diisostearyl malate, diisostearyl sebacate, dimethyl adipate, dimethyl oxalate, dimethyl phthalate, dioctyldodecyl adipate, Dioctyldodecyl Dimer Dilinoleate, Dioctyldodecyl Dodecanedioate, Dioctyldodecyl Fluoroheptyl Citrate, Dioctyldodecyl IPDI, Dioctyldodecyl Lauroyl Glutamate, Dioctyldodecyl Malate, Dioctyldodecyl Sebacate, Dioctyldodecyl Stearoyl Glutamate, dipentaerythrityl hexa $C_{5-9}$ acid esters, dipentaerythrityl hexa $C_{5-10}$ acid esters, dipropyl oxalate, pentaerythrityl tetra $C_{5-9}$ acid esters, pentaerythrityl tetra $C_{5-10}$ acid esters, tributyl citrate, tricaprylyl/capryl trimellitate, triethyl citrate, triethylene glycol dibenzoate, triethylene glycol rosinate, triethylhexyl citrate, triethylhexyl trimellitate, trimethylpentanediyl dibenzoate, trimethyl pentanyl diisobutyrate, polyglyceryl-6 pentacaprylate, polyglyceryl-10 pentahydroxystearate, polyglyceryl-10 pentaisostearate, polyglyceryl-10 pentalaurate, polyglyceryl-10 pentalinoleate, polyglyceryl-5 pentamyristate, polyglyceryl-4 pentaoleate, polyglyceryl-6 pentaoleate, polyglyceryl-10 pentaoleate, polyglyceryl-3 pentaricinoleate, polyglyceryl-6 pentaricinoleate, polyglyceryl-10 pentaricinoleate, polyglyceryl-4 pentastearate, polyglyceryl-6 pentastearate, polyglyceryl-10 pentastearate, sorbeth-20 pentaisostearate, sorbeth-30 pentaisostearate, sorbeth-40 pentaisostearate, sorbeth-50 pentaisostearate, sorbeth-40 pentaoleate, sucrose pentaerucate, and triacetin, combinations thereof. In some exemplary embodiments the hydrocarbon plug-preventing additive is selected from one or more of ispropyl myristate and diisopropyl sebacate.

In one or more embodiments, the plug-preventing additive comprises a polymeric ester. The polymeric ester can include one or more ester groups.

In some exemplary embodiments, the polymer chain includes a polyethylene glycol (PEG) chain, a polypropylene glycol (PPG), or a combination thereof. In one or more embodiments, the polymer chain includes up to about 12 PEG units, PPG units, or a combination thereof. In some exemplary embodiments, the polymer chain includes up to about 10 PEG units, PPG units, or a combination thereof. In some exemplary embodiments, the polymer chain includes up to about 8 PEG units, PPG units, or a combination thereof. In some exemplary embodiments, the polyether polymer chain includes from about 1 to about 12 PPG or PEG units, or from about 2 to about 8 PPG or PEG units, or a combination thereof.

Examples of polymeric esters include those that may be represented by the following formula

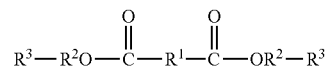

wherein $R^1$ is a linear or branched alkyl group having from 1 to 28 carbon atoms, each $R^2$, which may be the same or different, includes a polyether chain having up to about 12 PEG or PPG groups, or a combination thereof, and each $R^3$, which may be the same or different, includes an alkyl or alkylene group having from 1 to about 30 carbon atoms, and wherein each $R^3$ group is attached to $R^2$ via an ether linkage.

In some exemplary embodiments, $R^1$ includes up to about 20 carbon atoms, or up to about 10 carbon atoms, or up to about 8 carbon atoms. In some exemplary embodiments, $R^3$ may be represented by the formula $CH_3(CH_2)_zO-$, wherein z is an integer from 1 to about 21, or from 2 to about 17, or from 3 to about 15.

In one or more embodiments, the polymeric ester may be represented by the following formula

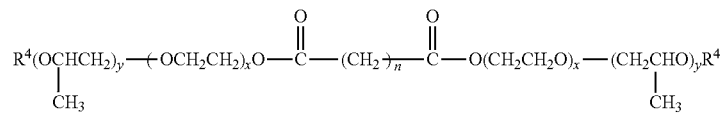

wherein $R^4$ includes a linear or branched, alkyl or alkylene group having from 1 to about 22 carbon atoms. In some exemplary embodiments, $R^4$ may be represented by the formula $CH_3(CH_2)_z-$, wherein some exemplary embodiments z is an integer from 1 to about 21, or from 2 to about 17, or from 3 to about 15. In some exemplary embodiments, n is an integer from 1 to about 20, or from 2 to about 10. In some exemplary embodiments x is an integer up to about 12, or up to about 10, or up to about 8, or is zero. In some exemplary embodiments, y is an integer up to about 12, or up to about 10, or up to about 8, or is zero. Examples of polymeric esters further include those that may be represented by the following formula

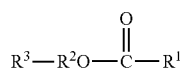

wherein R¹, R², and R³ are as described hereinabove.

Examples of polymeric esters include any of the above di-, tri, tetra-, penta-, or hexa-esters modified to include a PPG, PEG, or PPG/PEG polymer chain of the appropriate length. Specific examples include Di-PPG-3-ceteth-4 adipate, Di-PPG-2-myreth-10 adipate, Di-PPG-3-myristyl ether adipate, and PPG-2 myristyl ether propionate. In some exemplary embodiments, a mixture of one or more polymeric esters and one or more monomeric di-, tri-, tetra-, penta-, or hexa-esters may be employed as plug-preventing additives.

In other exemplary embodiments the plug-preventing comprises one or more diols, that is compounds with two hydroxyl groups. Plug-preventing additives that contain more or less hydroxyl groups (i.e., one hydroxyl group and three or more hydroxyl groups) are also within the purview of the exemplary embodiments disclosed herein. In one or more exemplary embodiments the diol is a $C_{6-10}$ alkane diol and/or a straight chain $C_{6-10}$ alkane diol. Non-limiting examples of suitable diols include 1,2-hexanediol, 1,2-octanediol (often referred to as caprylyl glycol), 1,9-nonanediol, 1,2-decanediol, 1,10-decanediol, or mixtures and blends thereof. It is envisioned that the diol can contain any other functional groups including, for example, esters, carboxylic acids, ethers, amides, amines, alkyl halides, phenyls, as well as other carbonyl-containing functional groups. In some exemplary embodiments, the plug-preventing agent contains at least one ester and/or at least one amide group. In some exemplary embodiments, the plug-preventing agent is selected from glyceryl caprylate/caprate (GCC) and cocoamide diethanolamine.

If separate from the humectant, the plug-preventing additive may be included in the sanitizing composition in an amount up to about 20.0 wt. %, or up to about 15.0 wt. %, or up to about 12.0 wt. %, or up to about 10.0 wt. %, or up to about 8.0 wt. % or up to about 5.0 wt. %, or up to about 3.0 wt. %, based on the total weight of the sanitizing composition. In some exemplary embodiments, the plug-preventing agent is included in an amount from about 0.001 wt. %, or from about 0.01 wt. %, or from about 0.05 wt. %, or from about 0.1 wt. %, or from about 0.5 wt. %, or from about 0.7 wt. %, or from about 1.0 wt. %, or from about 1.5 wt. %, or from about 2.0 wt. %, based on the total weight of the sanitizing composition. In one exemplary embodiment, the plug-preventing additive is included in an amount from about 0.05 to about 4.0 wt. %, or from about 0.1 to about 1.0 wt. %, or from about 0.15 to about 0.7 wt. %, or from about 0.2 to about 0.7 wt. %, based on the total weight of the sanitizing composition.

In certain embodiments, the plug-preventing additive is added to the composition as a solution or emulsion. That is, the plug-preventing additive can be premixed with a carrier to form a solution or emulsion, with the proviso that the carrier does not deliriously effect the ability of the sanitizing composition to sanitize and kill non-enveloped viruses. Examples of carriers include water, alcohol, glycols such as propylene or ethylene glycol, ketones, linear and/or cyclic hydrocarbons, triglycerides, carbonates, silicones, alkenes, esters such as acetates, benzoates, fatty esters, glyceryl esters, ethers, amides, polyethylene glycols and PEG/PPG copolymers, inorganic salt solutions such as saline, and mixtures thereof. It will be understood that, when the plug-preventing additive is premixed to form a plug-preventing additive solution or emulsion, the amount of solution or emulsion that is added to the sanitizing composition is selected so that the amount of plug-preventing additive falls within the ranges set forth hereinabove.

The sanitizing composition may further comprise one or more conditioning or moisturizing esters. Examples of such conditioning or moisturizing esters include cetyl myristate, cetyl myristoleate, and other cetyl esters, diisopropyl sebacate, and isopropyl myristate. The ester may be present in an amount of up to about 10.0 wt. %, or up to about 8.0 wt. %, or up to about 5.0 wt. %, or up to about 3.0 wt. %, or up to about 2.0 wt. %, or up to about 1.0 wt. %, based on the total weight of the sanitizing composition. In some exemplary embodiments, the moisturizing ester is present in an amount from about 0.001 wt. %, or from about 0.005 wt. %, or from about 0.01 wt. %, or from about 0.05 wt. %, or from about 0.1 wt. %, or from about 0.25 wt. %, or from about 0.5 wt. %, or from about 1.0 wt. %, based on the total weight of the sanitizing composition. In one exemplary embodiment, the moisturizing ester is present in an amount between 0.01 to 0.3 wt. %, based on the total weight of the sanitizing composition. In another exemplary embodiment, the moisturizing ester is present in an amount between 0.05 wt. % and 0.25 wt. %, based on the total weight of the sanitizing composition.

In one or more embodiments, the sanitizing composition may include one or more emulsifying agents. Examples of emulsifying agents include stearyl alcohol, sorbitan oleate trideceth-2, poloxamers, and PEG/PPG-20/6 dimethicone. In some exemplary embodiments, the emulsifying agent is present in an amount of up to about 10.0 wt. %, based on the total weight of the sanitizing composition. In other exemplary embodiments, the emulsifying agent is present in an amount of from about 0.1 to about 5.0 wt. %, or from about 0.5 to about 2.0 wt. %, based on the total weight of the sanitizing composition.

The sanitizing composition may further comprise one or more deposition enhancers. A suitable deposition enhancer works unidirectionally and will allow ingredients within the composition to penetrate deeper into the stratum corneum whilst preventing the loss of materials from the skin. Advantageously, the deposition enhancer provides a cosmetically acceptable skin feel to the formulation.

In one or more embodiments, the deposition enhancers include one or more of surfactants, bile salts and derivatives thereof, chelating agents, and sulphoxides.

Some examples of acceptable deposition enhancers include dimethyl sulphoxides (DMSO), DMA, DMF, 1-dodecylazacycloheptan-2-one (azone), pyrrolidones such as 2-Pyrrolidone (2P) and N-Methyl-2-Pyrrolidone (NMP), long-chain fatty acids such as oleic acid and fatty acids with a saturated alkyl chain length of about $C_{10}$-$C_{12}$, essential oils, terpenes, terpenoids, oxazolidinones such as 4-decyloxazolidin-2-one, sodium lauryl sulfate (SLS), sodium laureate, polysorbates, sodium glyacolate, sodium deoxycholate, caprylic acid, EDTA, phospholipids, $C_{12-15}$ Alkyl Benzoate, pentylene glycol, ethoxydiglycol, polysorbate-polyethylenesorbitan-monolaurate, and lecithin.

In one or more exemplary embodiments, the deposition enhancer is a quaternary ammonium compound such as polyquaternium-6,-7,-10,-22,-37,-39,-74 or -101.

The deposition enhancer may be included in the sanitizing composition in an amount from about 0.005 wt. % to about 10.0 wt. %, in other embodiments, from about 0.01 wt. % to about 5.0 wt. %, and in other embodiments, from about 0.05 wt. % to about 3.0 wt. %, based on the total weight of the sanitizing composition.

In one or more exemplary embodiments, the deposition enhancer comprises a hydroxy-terminated polyurethane compound chosen from polyolprepolymer-2, polyolprepolymer-14, and polyolprepolymer-15. Polyolprepolymer-2 is sometimes referred to as PPG-12/SMDI copolymer. The polyurethane compound may be present in the sanitizing composition in an amount from about 0.005 wt. % to about 5.0 wt. %, in other embodiments, from about 0.01 wt. % to about 3.0 wt. %, and in other embodiments, from about 0.05 wt. % to about 1.0 wt. %, based on the total weight of the sanitizing composition.

The sanitizing composition may further comprise one or more anti-irritants. Anti-irritants reduce signs of inflammation on the skin such as swelling, tenderness, pain, itching, or redness. There are three main types of anti-irritants, all of which are envisioned as being applicable in the exemplary embodiments described herein: (1) compounds that operate by complexing the irritant itself, (2) compounds that react with the skin to block reactive sites preventing the irritant from reacting directly with the skin, and (3) compounds that prevent physical contact between the skin and irritant.

Some exemplary examples of suitable anti-irritants include Aloe Vera, allantoin, anion-cation complexes, aryloxypropionates, azulene, carboxymethyl cellulose, cetyl alcohol, diethyl phthalate, Emcol E607, ethanolamine, glycogen, lanolin, N-(2-Hydroxylthyl) Palmitamide, N-Lauroyl Sarcosinates, Maypon 4C, mineral oils, miranols, Myristyl lactate, polypropylene glycol, polyvinyl pyrrolidone (PVP), tertiary amine oxides, thiodioglycolic acid, and zirconia. In one exemplary embodiment, the anti-irritant is avenanthrmides (*Avena Sativa* (oat), kernel oil, and glycerin) and niacinamide.

The anti-irritant may be included in the sanitizing composition in an amount up to about 10.0 wt. %, in other embodiments, from about 0.005 wt. % to about 3.0 wt. %, and in other embodiments, from about 0.01 wt. % to about 1.0 wt. %, based on the total weight of the sanitizing composition.

The sanitizing composition may further comprise a fragrance. Any scent may be used in the sanitizing composition including, but not limited to, any scent classification on a standard fragrance chart, such as floral, oriental, woody, and fresh. Exemplary scents include cinnamon, clove, lavender, peppermint, rosemary, thyme, thieves, lemon, citrus, coconut, apricot, plum, watermelon, ginger and combinations thereof.

The fragrance can be included in the sanitizing composition in an amount from about 0.005 wt. % to about 5.0 wt. %, in other embodiments, from about 0.01 wt. % to about 3.0 wt. %, and in other embodiments, from about 0.05 wt. % to about 1.0 wt. %, based on the total weight of the sanitizing composition. The fragrance can be any made of any perfume, essential oil, aroma compounds, fixatives, terpenes, solvents, and the like. In some exemplary embodiments, the essential oils may include, for example, one or more of Limonene, Citrus Aurantium *Dulcis* (Orange) Peel Oil, *Eucalyptus Globulus* Leaf Oil, *Citrus Grandis* (Grapefruit) Peel Oil, Linalool, *Litsea Cubeba* Fruit Oil, *Lavandula Hybrida* Oil, *Abies Sibirica* Oil, *Mentha Citrata* Leaf Extract, *Coriandrum Sativum* (Coriander) Fruit Oil, *Piper Nigrum* (Pepper) Fruit Oil, and *Canarium* Luzonicum Gum Nonvolatiles.

The sanitizing composition may further comprise a wide range of optional ingredients that do not deleteriously affect the composition's ability to stimulate AMP production and/or activity and that do not deleteriously affect the composition's ability to restore the microbial balance on the surface of the skin. The CTFA International Cosmetic Ingredient Dictionary and Handbook, Eleventh Edition 2005, and the 2004 CTFA International Buyer's Guide, both of which are incorporated by reference herein in their entirety, describe a wide variety of non-limiting cosmetic and pharmaceutical ingredients commonly used in the skin care industry, that are suitable for use in the compositions of the exemplary embodiments described herein. Examples of these functional classes include: abrasives, anti-acne agents, anticaking agents, antioxidants, binders, biological additives, bulking agents, chelating agents, chemical additives; colorants, cosmetic astringents, cosmetic biocides, denaturants, drug astringents, emulsifiers, external analgesics, film formers, fragrance components, opacifying agents, plasticizers, preservatives (sometimes referred to as antimicrobials), propellants, reducing agents, skin bleaching agents, skin-conditioning agents (emollient, miscellaneous, and occlusive), skin protectants, solvents, surfactants, foam boosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials useful herein that are well known to one of ordinary skill in the art include solubilizing agents, sequestrants, keratolytics, topical active ingredients, and the like.

The sanitizing compositions exhibit a pH in the range of from about 2.5 to about 12.0, or a pH in the range of from about 3.5 to about 8, or in the range of from about 4.0 and about 7.5. When necessary, a pH adjusting agent or constituent may be used to provide and/or maintain the pH of a composition. Exemplary pH adjusting agents include, but are not limited to, organic acids, such as citric acid, lactic acid, formic acid, acetic acid, proponic acid, butyric acid, caproic acid, oxalic acid, maleic acid, benzoic acid, carbonic acid, and the like.

The form of the composition of the exemplary embodiments described herein is not particularly limited. In one or more embodiments, sanitizing compositions of the exemplary embodiments described herein may be formulated as a foamable composition, a thickened gel composition, a sprayable liquid, a rinse, or may be applied to a wipe.

In one or more embodiments, the sanitizing composition of the exemplary embodiments described herein may be in the form of a thickened gel, with the inclusion of one or more thickeners and optionally one or more stabilizers. Examples of thickeners and stabilizers include hydroxyethyl cellulose hydroxypropyl cellulose, methyl cellulose, carboxymethyl cellulose, and ammonium acryloyldimethyltaurate/VP copolymer. Where the thickener or stabilizer is starch-based, the thickener or stabilizer may be present in an amount of up to about 10.0 wt. %, or in an amount of from about 0.1 to about 5.0 wt. %, or from about 0.2 to about 1.0 wt. %, based on the total weight of the sanitizing composition. Where the thickener or stabilizer is a synthetic polymer, the thickener or stabilizer may be present in an amount of up to about 15.0 wt. %, or from about 0.05 to about 5.0 wt. %, or from about 0.1 to about 1.0 wt. %, based on the total weight of the sanitizing composition.

In one or more exemplary embodiments, the sanitizing composition may be thickened with polyacrylate thickeners such as those conventionally available and/or known in the art. Examples of polyacrylate thickeners include carbomers, acrylates/$C_{10-30}$ alkyl acrylate crosspolymers, copolymers of acrylic acid and alkyl ($C_5$-$C_{10}$) acrylate, copolymers of acrylic acid and maleic anhydride, and mixtures thereof. In one or more embodiments, the gel composition includes an effective amount of a polymeric thickener to adjust the viscosity of the gel to a viscosity range of from about 1000 to about 65,000 centipoise (cP). In one embodiment, the viscosity of the gel is from about 5000 to about 35,000 cP, and in another embodiment, the viscosity is from about 10,000 to about 25,000 cP. The viscosity is measured by a Brookfield RV Viscometer using RV and/or LV Spindles at 22° C.+/−3° C.

As will be appreciated by one of skill in the art, the effective amount of thickener will vary depending on a number of factors, including the amount of alcohol and other ingredients in the gel composition. In one or more embodiments, an effective amount of thickener is at least about 0.01 wt. %, based on the total weight of the gel composition. In other embodiments, the effective amount is at least about 0.02 wt. %, or at least about 0.05 wt. %, or at least about 0.1 wt. %. In some exemplary embodiment, the effective amount of thickener is at least about 0.5 wt. %, or at least about 0.75 wt. %, based on the total weight of the gel composition. In one or more embodiments, the compositions according to the exemplary embodiments described herein comprise up to about 10.0 wt. % of a polymeric thickener, based on the total weight of the gel composition. In certain embodiments, the amount of thickener is from about 0.01 to about 1.0 wt. %, or from about 0.02 to about 0.4 wt. %, or from about 0.05 to about 0.3 wt. %, based on the total weight of the gel composition. The amount of thickener may be from about 0.1 to about 10.0 wt. %, or from about 0.5% to about 5.0 wt. %, or from about 0.75 to about 2.0 wt. %, based on the total weight of the gel composition.

In one or more embodiments, the gel composition may further comprise a neutralizing agent. Examples of neutralizing agents include amines, alkanolamines, alkanolamides, inorganic bases, amino acids, including salts, esters and acyl derivatives thereof. Exemplary neutralizing agents include triethanolamine, sodium hydroxide, monoethanolamine and dimethyl stearylamine. Other neutralizing agents are also known, such as $HO(C_mH_{2m})_2NH$, where m has the value of from 2 to 3, and aminomethyl propanol, aminomethyl propanediol, and ethoxylated amines, such as PEG-25 cocamine, polyoxyethylene (5) cocamine (PEG-5 cocamine), polyoxyethylene (25) cocamine (PEG-25 cocamine), polyoxyethylene (5) octadecylamine (PEG-S stearamine), polyoxyethylene (25) octadecylamine (PEG-25 stearamine), polyoxyethylene (5) tallowamine (PEG-5 tallowamine), polyoxyethylene (15) oleylamine (PEG-15 oleylamine), polyethylene (5) soyamine (PEG-5 soyamine), and polyoxyethylene (25) soyamine (PEG-15 soyamine). A number of these are commercially available under the trade name of Ethomeen® from Akzo Chemie America, Armak Chemicals of Chicago, Ill.

In some exemplary embodiments the neutralizing agent includes at least one of sodium hydroxide or sodium hydroxide precursors. Solutions of sodium hydroxide in water are non-limiting examples of neutralizers containing sodium hydroxide.

The neutralizing agent is employed in an effective amount to neutralize a portion of the carboxyl groups of the thickening agent, and produce the desired pH range. The pH of un-neutralized thickening agent dispersed in water is generally acidic. For example, the pH of Carbopol® polymer dispersions is approximately in the range of 2.5 to 3.5, depending upon the polymer concentration. An effective amount of neutralizing agent, when added to the thickener dispersion, adjusts the pH to a desired range of about 4.1 to 4.8, or of about 4.2 to 4.6. The amount of neutralizing agent necessary to effect this pH range will vary depending upon factors such as the type of thickening agent, the amount of thickening agent, etc. However, in general, amounts less than 1.0% by weight and ranging from about 0.001 to about 0.3 wt. %, based on the total weight of the sanitizing composition of the neutralizing agent are considered sufficient and effective.

In one or more embodiments, the sanitizing composition is formulated as a foamable composition. One or more foam agents may optionally be included in the foamable composition.

Any foaming agent conventionally known and used may be employed in the sanitizing composition. In one or more embodiments, the foam agent comprises a non-ionic foam agent such as decyl glucoside or an amphoteric foam agent such as cocamidopropylbetaine. In one or more embodiments, the amount of nonionic or amphoteric foam agent is from about 0.5 to about 3.5 wt. %, in other embodiments from about 1.0 to about 3.0 wt. %, based on the total weight of the sanitizing composition. In one or more embodiments, the amount of decyl glucoside or cocamidopropylbetaine is from about 0.5 to about 3.5 wt. %, in other embodiments from about 1.0 to about 3.0 wt. %, based on the total weight of the sanitizing composition.

In some exemplary embodiments, the foaming agents include one or more of silicone glycol and fluorosurfactants. Silicone glycols may be generally characterized by containing one or more Si—O—Si linkages in the polymer backbone. Silicone glycols include organopolysiloxane dimethicone polyols, silicone carbinol fluids, silicone polyethers, alkylmethyl siloxanes, amodimethicones, trisiloxane ethoxylates, dimethiconols, quaternized silicone glycols, polysilicones, silicone crosspolymers, and silicone waxes.

Examples of silicone glycols include dimethicone PEG-7 undecylenate, PEG-10 dimethicone, PEG-8 dimethicone, PEG-12 dimethicone, perfluorononylethyl carboxydecal PEG 10, PEG-20/PPG-23 dimethicone, PEG-11 methyl ether dimethicone, bis-PEG/PPG-20/20 dimethicone, silicone quats, PEG-9 dimethicone, PPG-12 dimethicone, fluoro PEG-8 dimethicone, PEG-23/PPG-6 dimethicone, PEG-20/PPG-23 dimethicone, PEG 17 dimethicone, PEG-5/PPG-3 methicone, bis-PEG-18 methyl ether dimethyl silane, bis-PEG-20 dimethicone, PEG/PPG-20/15 dimethicone copolyol and sulfosuccinate blends, PEG-8 dimethicone\dimmer acid blends, PEG-8 dimethicone\fatty acid blends, PEG-8 dimethicone\cold pressed vegetable oil\polyquaternium blends, random block polymers and mixtures thereof.

The amount of silicone glycol foam agent is not particularly limited, so long as an effective amount to produce foaming is present. In certain embodiments, the effective amount to produce foaming may vary, depending on the amount of alcohol and other ingredients that are present. In one or more embodiments, the composition includes at least about 0.002 wt. % of silicone glycol foam agent, based on the total weight of the composition. In another embodiment, the composition includes at least about 0.01 wt. % of silicone glycol foam agent, based on the total weight of the sanitizing composition. In yet another embodiment, the composition includes at least about 0.05 wt. % of silicone glycol foam agent, based on the total weight of the sanitizing composition.

In some exemplary embodiments, the foam agent is present in an amount of from about 0.002 to about 4.0 wt. %, or in an amount of from about 0.01 to about 2.0 wt. %, based on the total weight of the composition. It is envisioned that higher amounts may also be effective to produce foam. All such weights as they pertain to listed ingredients are based on the active level, and therefore, do not include carriers or by-products that may be included in commercially available materials, unless otherwise specified.

In other embodiments, it may be desirable to use higher amounts of foam agent. For example, in certain embodiments where the foaming composition of the exemplary embodiments described herein includes a cleansing or sanitizing product that is applied to a surface and then rinsed off, higher amounts of foam agent may be employed. In these embodiments, the amount of foam agent is present in amounts up to about 35.0 wt. %, based on the total weight of the sanitizing composition.

The sanitizing composition of the exemplary embodiments described herein may be formulated as an aerosol or non-aerosol foamable composition. In some exemplary embodiments the sanitizing composition is dispensed from an unpressurized or low-pressure dispenser which mixes the composition with air.

In one or more embodiments, the viscosity of the non-aerosol foamable composition is less than about 100 mPas, in one embodiment less than about 50 mPas, and in another embodiment less than about 25 mPas.

The composition of the exemplary embodiments described herein may be employed in any type of dispenser typically used for gel products, for example pump dispensers. A wide variety of pump dispensers are suitable. Pump dispensers may be affixed to bottles or other free-standing containers. Pump dispensers may be incorporated into wall-mounted dispensers. Pump dispensers may be activated manually by hand or foot pump, or may be automatically activated. Useful dispensers include those available from GOJO Industries under the designations NXT®, TFX™, DPX™, FMX™, ADX™ LTX™, and CXT™ as well as traditional bag-in-box dispensers. Examples of dispensers are described in U.S. Pat. Nos. 5,265,772, 5,944,227, 6,877, 642, 7,028,861, 7,611,030, 7,621,426, 8,740,019, 8,991,657, 9,027,790, 9,073,685, 9,101,250, and 9,204,767, all of which are incorporated herein by reference. In one or more embodiments, the dispenser includes an outlet such as a nozzle, through which the composition is dispensed. In some exemplary embodiments, the sanitizing composition is used in dispensers that employ foaming pumps, which combine ambient air or an inert gas and the composition in a mixing chamber and pass the mixture through a mesh screen.

In one or more embodiments, the sanitizing composition is integrated into wipe composition. Wipe compositions in accordance with the exemplary embodiments described herein include at least one alcohol, a $C_{1-10}$ alkanediol enhancer, and are applied to a wipe substrate. In some exemplary embodiments, the wipe composition is alcohol-free.

Wipe substrates used in antimicrobial wipes are further described in U.S. Pat. Nos. 5,686,088, 6,410,499, 6,436,892, 6,495,508, 6,844,308, 9,096,821, which are incorporated herein by reference. In one or more embodiments, the wipe may comprise a laminate formed by spunbonding/meltblowing/spunbonding (SMS). Generally, an SMS material contains a meltblown web sandwiched between two exteriors spunbond webs. SMS materials are further described in U.S. Pat. Nos. 4,041,203, 5,169,706, 5,464,688, and 4,766,029, and are commercially available, for example from Kimberly-Clark Corporation under marks such as Spunguard 7 and Evolution 7. The SMS laminate may be treated or untreated.

In other exemplary embodiments, the sanitizing composition is formulated as a spray. In some exemplary embodiments, the spray is a nasal spray that is designed to be used in the nose. The particular delivery method of the nasal spray is not particularly limited. Exemplary delivery methods and base compositions which are envisioned as suitable for the exemplary embodiments disclosed herein are disclosed in U.S. Pat. Nos. 8,053,005; 8,158,163; 8,778,415; 8,999,406; and 9,463,212, all to Global Life Technologies Corp., all of which are incorporated herein by reference. In some exemplary embodiments, the nasal spray is used in a hospital to treat some or all admitted patients. In some exemplary embodiments, hospital and out-patient healthcare employees are treated with the nasal spray. In some exemplary embodiments, patients with a history or recurrent folliculitis, furunculosis, and/or staph aureus are treated with the nasal spray. In still other exemplary embodiment, family members of patients suffering from these conditions are treated with the nasal spray.

In some exemplary embodiments, the nasal spray sanitizing composition comprises one or more $C_{1-8}$ alcohols and an active ingredient. In some exemplary embodiments, the active ingredient comprises one or more of a probiotic, a probiotic derivative, and a prebiotic. In some exemplary embodiments, the active ingredient comprises one or more probiotics. In some exemplary embodiments, the probiotic is a topical probiotic. By topical probiotic it is meant a probiotic that is designed to be used on the skin or other part of a mammalian body. In some exemplary embodiments, the nasal spray is essentially free or completely free of oral probiotics. Oral probiotics are those that are meant to be ingested. By "essentially free of oral probiotics" it is meant that the nasal spray contains no greater than 5.0 wt. %, preferably no greater than 1.0 wt. %, and more preferably no greater than 0.5 wt. % peroxides. In some exemplary embodiments, the nasal spray sanitizing composition comprises various fragrances. In some exemplary embodiments, application of the nasal spray reduces pathogen binding in the nose by an amount that is statistically significant, as compared to an otherwise identical nasal spray without the active ingredient.

In some exemplary embodiments, the nasal spray kills staph bacteria, such as that associated with and responsible for methicillin-resistant *Staphylococcus Aureus* (MRSA). In some exemplary embodiments, the nasal spray with alcohol and active ingredient helps to reestablish the healthy normal nasal flora biome. In some exemplary embodiments, the nasal spray provides efficacy against pathogenic bacteria and does not promote bacterial-resistance developing even with extended use. In some exemplary embodiments, the nasal spray helps to fight and defend against pathogens associated with of *Clostridium Difficile* infections of the intestine, *C. difficile*, MRSA, folliculitis, furunculosis, and staph *aureus*.

In some exemplary embodiments, the sanitizing composition decreases the production and/or activity of pro-inflammatory factors such as interleukins, including interleukin-8 (IL-8). Over-expression of IL-8 is a biomarker of skin irritation. IL-8 is associated with inflammation and plays a role in colorectal cancer. In some exemplary embodiments, a sanitizing composition comprising up to about 15.0 wt. % of the active ingredient in water is able to reduce the relative production and/or activity of pro-inflammatory factors by at least about 50%, or at least about 70%, or at least about 78%, as compared to an otherwise identical control composition without the active ingredient. In other exemplary embodiments, a sanitizing composition comprising up to about 15.0 wt. % of an active ingredient in ethanol is able to reduce the relative production and/or activity of pro-inflammatory factors by at least about 15%, or at least about 25%, or at least about 30%, as compared to an otherwise identical control composition without the active ingredient.

In some exemplary embodiments, the sanitizing composition increases the expression of Involucrin. Involucrin is a protein component of human skin and is encoded in humans by the IVL gene. In some exemplary embodiments, a sanitizing composition comprising up to about 15.0 wt. % of an active ingredient is able to increase the relative Involucrin production and/or activity by at least 50%, or at least 70%, or at least 90% or at least 100%, as compared to an otherwise identical control composition not including the active ingredient.

In some exemplary embodiments, the sanitizing composition increases the production and/or activity of cadherins. In some exemplary embodiments, the increased cadherins are desmosomals, such as DCS3. In some exemplary embodiments, a sanitizing composition comprising up to about 15.0 wt. % of an active ingredient is able to increase the relative production and/or activity cadherins, such as DCS3 by at least about 25%, or at least 35%, or at least 50%, or at least 57%, as compared to an otherwise identical control composition not including the active ingredient.

In some exemplary embodiments, a sanitizing composition comprising up to about 15.0 wt. % of an active ingredient increases the production and/or activity of defensins, such as HBD-2. HBD-2 is a low molecular weight AMP produced by epithelia cells and is encoded by the DEFB4 gene. It exhibits potent antimicrobial activity against Gram-negative bacteria and *Candida*. In some exemplary embodiments, a sanitizing composition comprising up to about 15.0 wt. % of an active ingredient in water is able to increase the relative production and/or activity of defensins, such as HBD-2 by at least about 25%, or at least about 35%, or at least about 45%, or at least about 55%, or at least about 65%, or at least about 75%, or at least about 90%, or at least about 100%, or at least about 125%, or at least 140%, as compared to an otherwise identical control composition without the active ingredient.

EXAMPLES

The following examples are included for purposes of illustration and are not intended to limit the scope of the methods described herein.

Example 1

Sanitizing compositions with Bonicel™ were tested for their ability to decrease production and/or activity of Interleukin 8 (IL-8 or CXCL8), which is a chemokine and proinflammatory cytokine produced by macrophages and other cell types such as epithelial cells. IL-8 is secreted from keratinocytes in skin in response to inflammatory stimuli.

For Control A, human dermal keratinocytes were left untreated. No irritation is expected, and therefore Control A provides a baseline (set as 0). For Control B, IL-8 is induced in human dermal keratinocytes by applying a surfactant mixture that is a combination of sodium laureth sulfate and polyquaternium-10 (set as 100%). Samples of Bonicel™ in both a water composition and ethanol composition were tested for their ability to alter IL-8 expression. For all other samples, the human dermal keratinocytes are co-treated with the surfactant mixture and a composition containing indicated concentration of Bonicel™. Decreased IL-8 expression reflects an ingredient's anti-irritation activity. In order to carry out the test method, an assay kit was employed that was obtained from R&D Systems: Human CXCL8/IL-8 Duoset ELISA Kit (DY208). ELISA was performed after overnight treatment using by applying 100 µl/well of culture medium according to the manufactory instruction of the ELISA kit. The results were measured using a colorimeter, absorbance was measured at 450 nanometers (nm) within 30 minutes. Wavelength correction was set to 570 nm.

The results showed a sanitizing composition with Bonicel™ was able to reduce the relative IL-8 production and/or activity. A relative decrease in IL-8 production and/or activity of about 78% was observed for a sanitizing composition with 1.0% Bonicel™, water, and a surfactant, as compared to a control composition with water and a surfactant. A relative decrease in IL-8 production and/or activity of 30% was observed for a sanitizing composition with 1.0% Bonicel™, ethanol, and a surfactant, as compared to a control composition with ethanol and a surfactant. The results are depicted graphically in FIG. 1.

Example 2

An in vitro study was conducted to study a sample of Bonicel™ specifically for its ability to increase production and/or activity of Involucrin.

Neonatal Human Epidermal Keratinocytes (NHEK; Life Technology, Grand Island, N.Y., USA) were cultured with keratinocyte growth medium (KGM, Medium 154: M-154-500 Life Technology with supplements S-001, Life Technologies). Keratinocytes were treated with the sample compositions in a 6-well plate overnight. After washing with cold phosphate-buffered saline (PBS), total RNAs were prepared from each well. Real-Time Quantitative Reverse Transcription PCR (qRT-PCR) was performed to detect the target genes (Involucrin) expression level using a One-step TaqMan® RT-PCR kit (Life Technologies).

Figure 2:
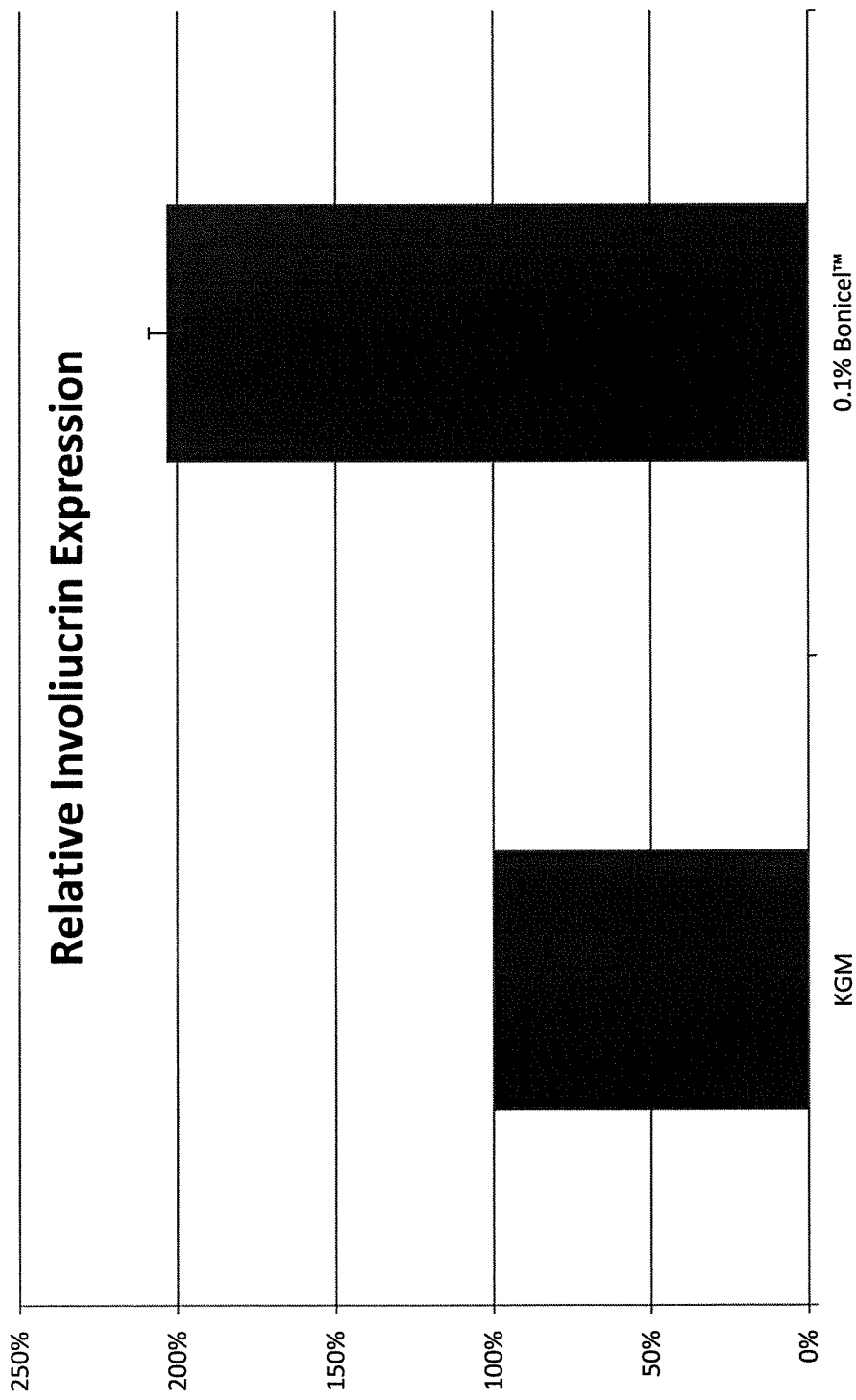
FIG. 2 illustrates an exemplary graph of the Involiucrin expression in compositions containing 1.0 wt. % Bonicel™ compared to a control.

The results showed that Bonicel™ increased the relative production and/or activity of Involucrin. A relative increase in Involucrin production and/or activity of about 103% was observed for 0.1% Bonicel™ as compared to the KGM medium control culture. This increase shows that Bonicel™ can stimulate Involucrin production and/or activity in keratinocyte to promote skin keratinocyte differentiations and improve skin barrier function. The results are depicted graphically in FIG. 2.

Example 3

An in vitro study was conducted to study a sample of Bonicel™ specifically for its ability to increase production and/or activity of desmocollin-3 (DSC3).

Neonatal Human Epidermal Keratinocytes (NHEK; Life Technology, Grand Island, N.Y., USA) were cultured with keratinocyte growth medium (KGM, Medium 154: M-154-500 Life Technology with supplements S-001, Life Technologies). Keratinocytes were treated with the sample compositions in a 6-well plate overnight. After washing with cold phosphate-buffered saline (PBS), total RNAs were prepared from each well. Real-Time Quantitative Reverse Transcription PCR (qRT-PCR) was performed to detect the target genes (DSC3) expression level using a One-step TaqMan® RT-PCR kit (Life Technologies).

Figure 3:
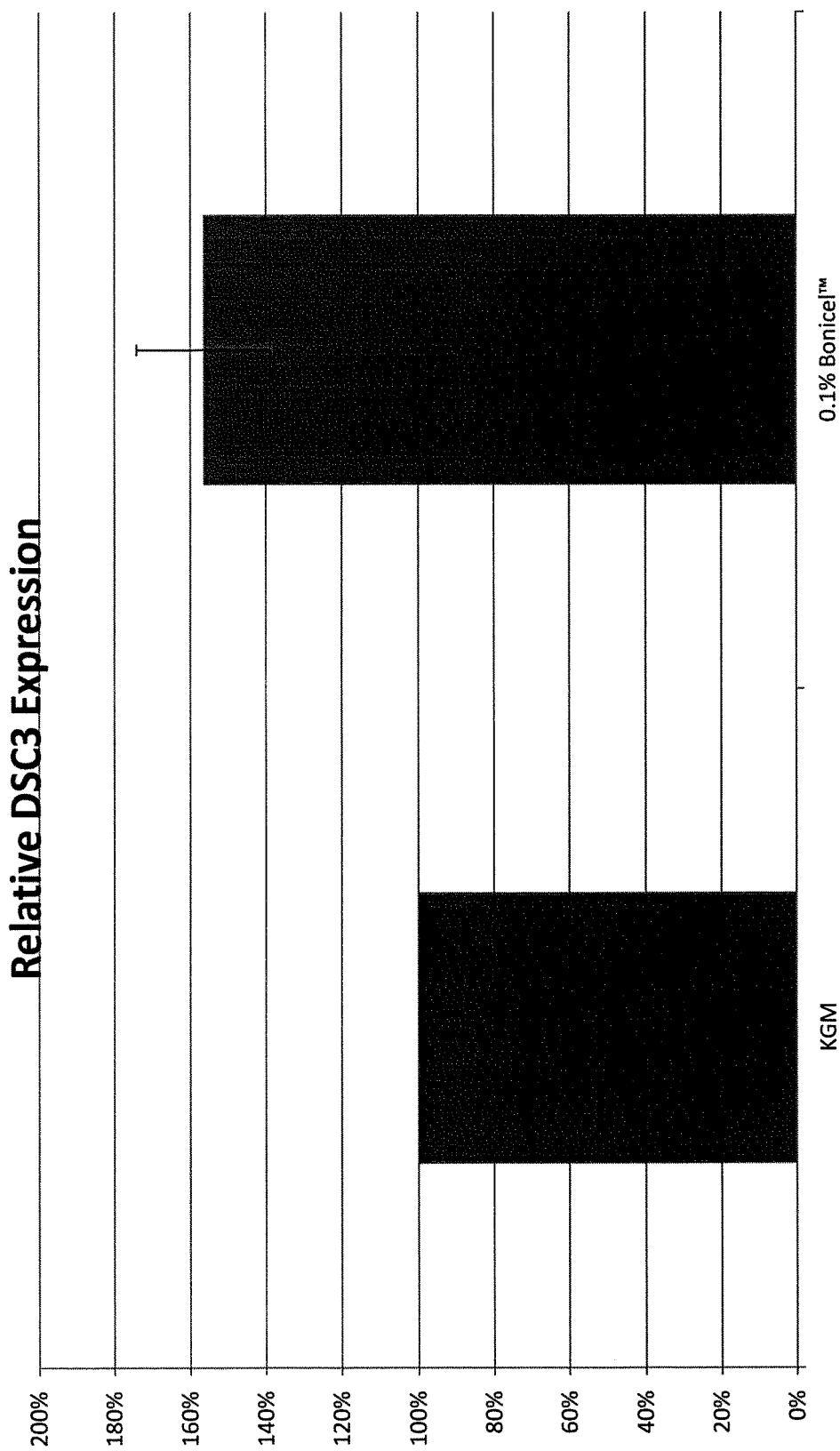
FIG. 3 illustrates an exemplary graph of the DSC3 expression in compositions containing 0.1 wt. % Bonicel™ compared to a control.

The results showed that Bonicel™ increased the relative production and/or activity of DSC3. A relative increase in DCS3 production and/or activity of about 57% was observed for 0.1% Bonicel™ as compared to the KGM medium culture. This increase shows that Bonicel™ can stimulate the skin junction biomarker DSC3 production and/or activity in keratinocytes to improve skin barrier function. The results are depicted graphically in FIG. 3.

Example 4

In vitro studies were also run with Bonicel™ specifically to determine its ability to simulate production and/or activity of human beta-defensin 2 (HBD-2). Bonicel™ was tested at concentrations of both 0.1% and 1.0% and in each of dermatological carriers, ethanol and water.

Neonatal Human Epidermal Keratinocytes (NHEK; Life Technology, Grand Island, N.Y., USA) were cultured with keratinocyte growth medium (KGM, Medium 154: M-154-500 Life Technology with supplements S-001, Life Technologies). NHEK were seeded into 96-well plates at a density of 10000 cells in 200 μl medium per well. After 48 hours, the cells were incubated with varying concentrations of each ingredient solution in a culture medium (KGM) overnight (16 hours) at 37° C., 5% $CO_2$ and 95% humidity at four replicates for each concentration. Each of these active ingredients was tested at the different concentration of weight percents based on the weight of the total culture. Each of these compositions was compared to a control culture medium.

HBD-2 was detected using HBD-2 ELISA developing kits (commercially available from Peprotech). ELISA were performed according to the manufactory instructions of each kit by adding 100 μl/well of culture medium after overnight treatment. The substrate of ELISA reaction was using the substrate reagent from R&D Systems (DY999), and the reactions were stopped by adding 50 μl of IN $H_2SO_4$ in each well. The results were measured using a colorimeter, absorbance was measured at 450 nanometers (nm) within 30 minutes. Wavelength correction was set to 570 nm. The concentration of each sample was calculated using ELISA standard curve.

Figure 4:
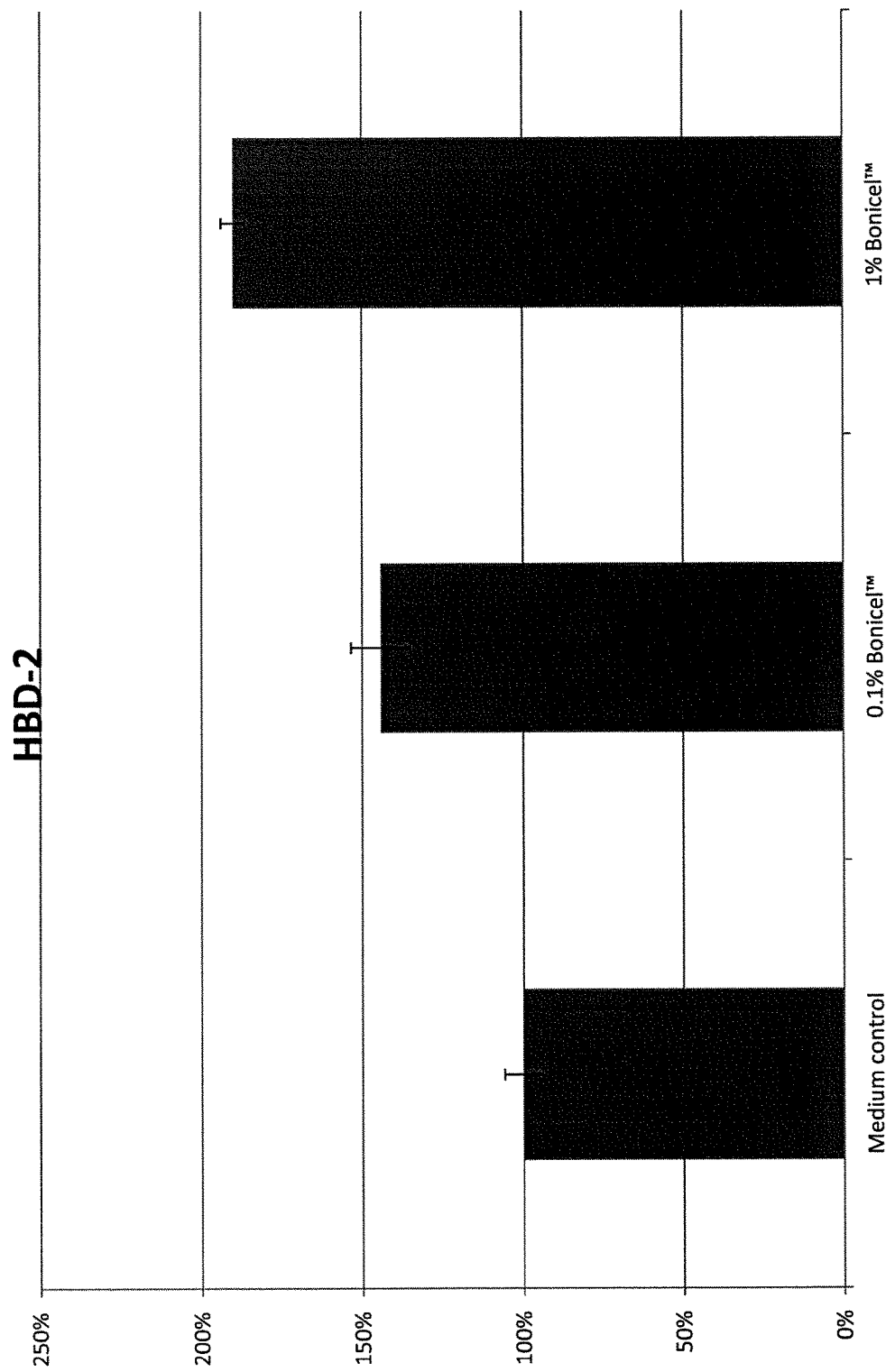
FIG. 4 illustrates an exemplary graph of the HBD-2 expression in compositions containing 0.1 wt. % Bonicel™ and 1.0 wt. % Bonicel™ compared to a control.
Figure 5:
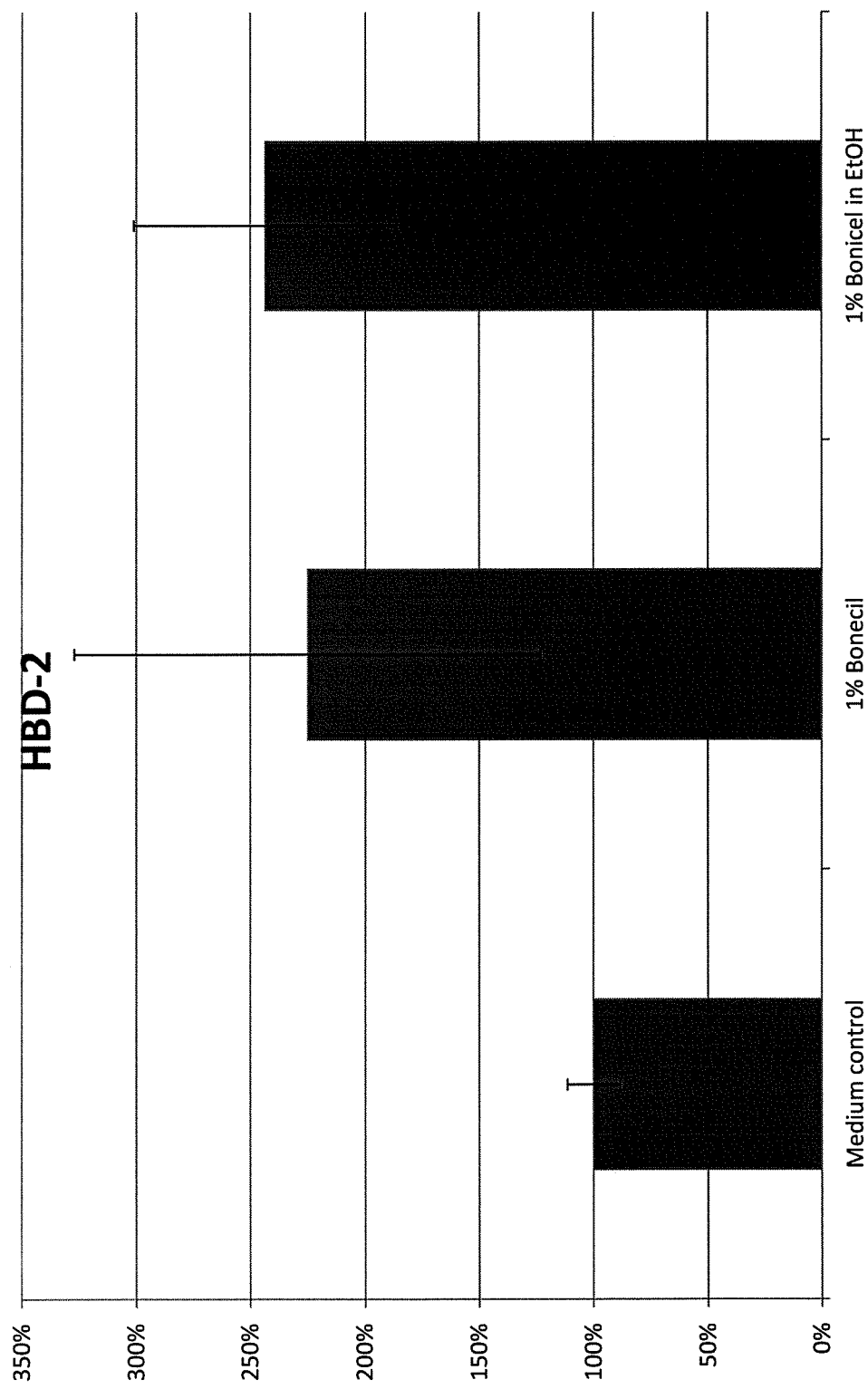
FIG. 5 illustrates an exemplary graph of the HBD-2 expression in compositions containing 0.1 wt. % Bonicel™ and 1.0 wt. % Bonicel™ that have been in contact with ethanol compared to a control.

The results showed the Bonicel™ is able to increase the production and/or activity of HBD-2 both in a composition with water and in a composition that had been in contact with ethanol. Relative increases in HBD-2 production and/or activity of about 44% and about 90% were observed for 0.1% Bonicel™ in a composition with water and 1.0% Bonicel™ in a composition with water, respectively. Additionally relative increases in HBD-2 production and/or activity of about 125% and about 144% were observed for 0.1% Bonicel™ in a composition that had been in contact with ethanol and 1.0% Bonicel™ in a composition that had been in contact with ethanol, respectively. From these results, it is also apparent that Bonicel™ does not lose its ability to increase the production and/or activity of HBD-2 and in fact, the effectiveness of the composition actually increased substantially when combined with the ethanol. The results for Bonicel™ in a water composition are depicted in FIG. 4 and the results for Bonicel™ that had been in contact with ethanol composition are depicted in FIG. 5.

Example 5

The effect of exemplary sanitizing compositions was investigated for pathogen blocking potential. Methicillin resistant *Staphylococcus aureus* strain Mu50 ATCC 33591, *Escherichia coli* strain K12 was tested against the following exemplary topical compounds: DMEM (cell culture medium, control), 100 nM dexamethasone (DEX, control steroidal anti-inflammatory), 0-5% Ecoskin (α-gluco-oligosaccharide, fructo-oligosaccharide and inactivated *Lactobacillus*), 0-5% *Bacillus* ferment, and 0-5% of a prebiotic blend of inulin and fructo-oligosaccharide.

Differentiated colonic epithelial cells were treated with the topical compounds and a bacterial strain was then added individually. The microbe was grown to the mid-log phase in an acceptable medium and the concentration adjusted so that the amount of bacteria added to the wells was approximately 100 microbes per well (in a 96 well tray with total volume of 100 uL). The cells were then incubated with each bacterial strain for one hour. A Gentamicin protection assay was used to determine adhered and invaded bacteria. Polymerase chain reaction (PCR) using 16S gene primers was used to determine the number of adhered bacteria, as well as the number of bacteria that invaded into the host cells.

Figure 6:
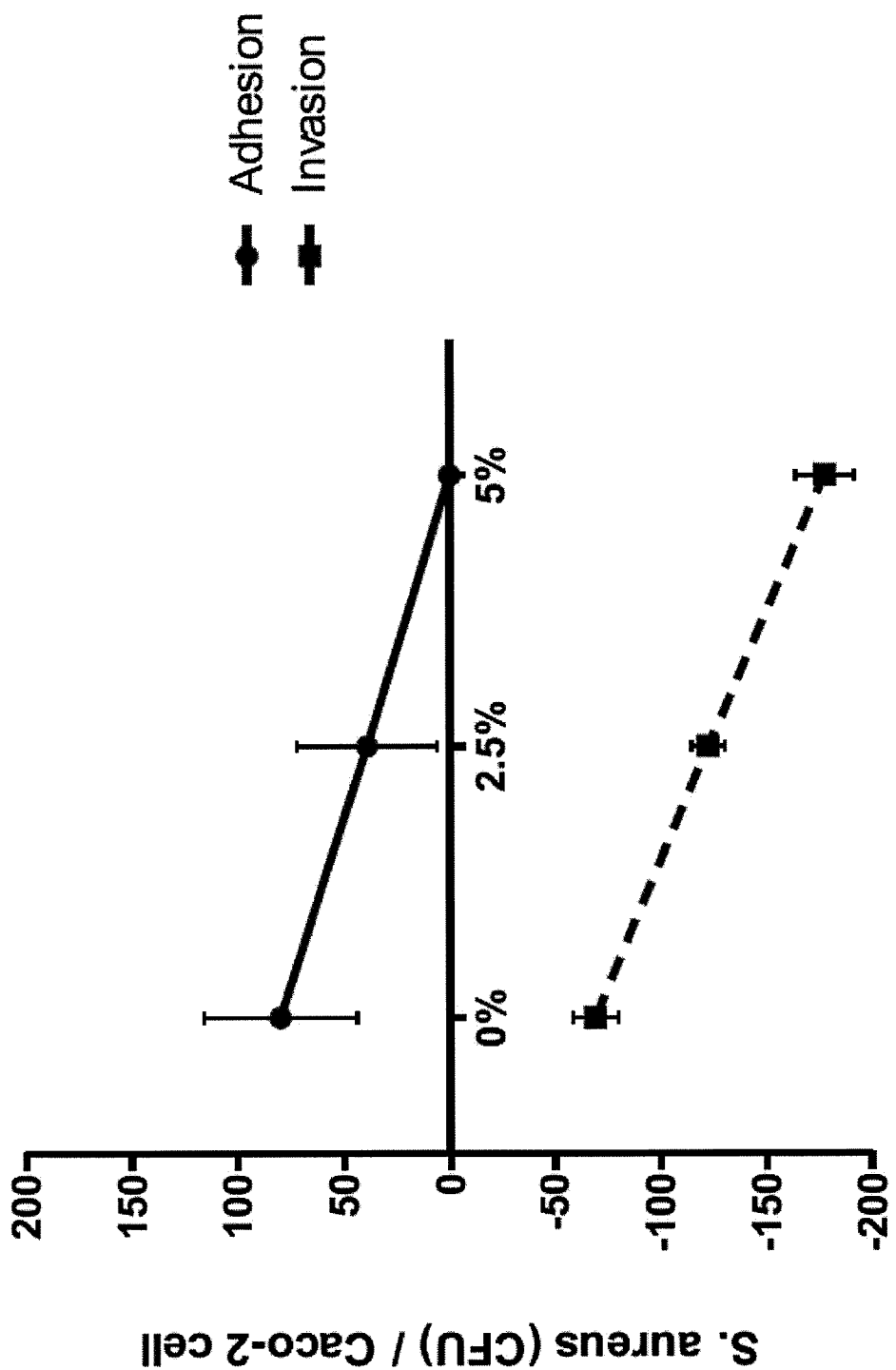
FIG. 6 illustrates an exemplary graph of the response of *Staphylococcus aureus* adhesion and invasion potential when treated with a probiotic *Bacillus* ferment.

FIG. 6 illustrates the dose-dependent response of *Staphylococcus aureus* adhesion and invasion potential. *Bacillus* ferment had a consistent increase in the dose response. Particularly, 5% *Bacillus* ferment resulted in the lowest adhesion occurrence overall.

Example 6

The effect of exemplary sanitizing compositions was investigated for its ability to kill more transient bacteria than resident. Each test group contained 6 participants for the extended use impacts experiment. Each day, prior to testing, both hands were washed with a bland soap to remove the transient bacteria that existed on the participant's hands before they entered the laboratory. In the immediate impact experiment, hands were intentionally contaminated by adding a mixture of *Serratia marsescens* and *Enterococcus faecalis* to the palmar side of the hands and rubbing for 30 seconds. Hand bacteria were sampled using a glove juice method followed by plated onto CHROMAgar™ orientation plates with and without antibiotics. One hand was sampled before application of each test article and then the other hand was sampled to obtain the post-hygiene use measurement. CFU counts before and after were compared to obtain LogioCFU reduction values. In the extended use experiment, both hands were sampled using the glove juice method before and then again after 12 days of use of either a hand sanitizer or a topical antibiotic cream five times a day, or after avoiding all exposure to antimicrobials. Plate counts of viable bacteria were obtained and the composition of the hand bacteria was determined via 16S rRNA gene sequencing of DNA extracted from the glove juice solutions before and after the 12 days of the trial.

Figure 7:
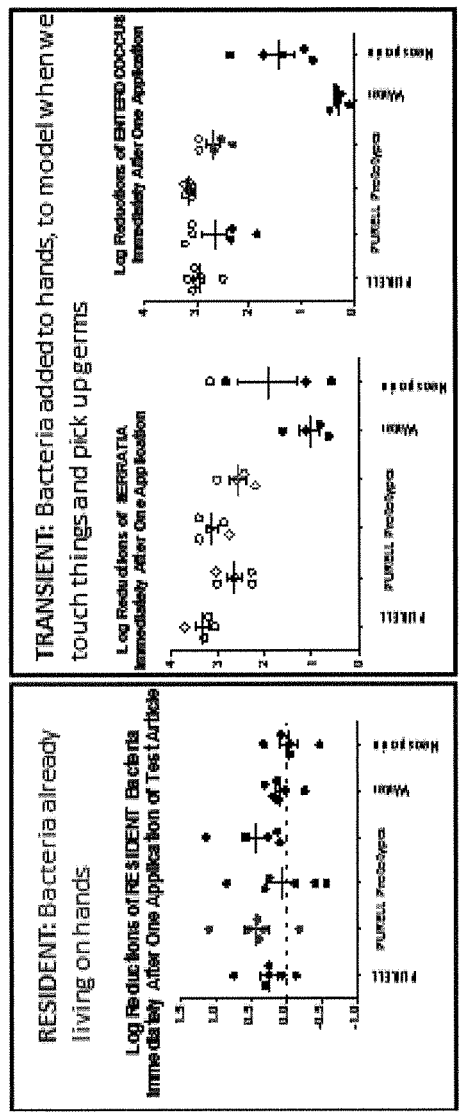
FIG. 7 graphically illustrates the affinity of a 1.0% Bonicel™ sanitizer to kill more transient bacteria than resident bacteria.

As illustrated in FIG. 7, the results indicated that a 1.0% Bonicel™ composition killed significantly more transient bacteria than resident bacteria, thereby restoring the skin's natural balance.

Although embodiments of the invention have been described herein, it should be appreciated that many modifications can be made without departing from the spirit and scope of the general inventive concepts. All such modifications are intended to be included within the scope of the invention, which is to be limited only by the following claims.

What is claimed is:

1. A sanitizing composition for restoring skin's natural balance of bacteria, the composition comprising:
   from about 0.005 wt. % to about 15.0 wt. % of an active ingredient selected from the group consisting of one or more strains of *Lactobacillus, Clostridia, Saccharomyces, Lactococcus, Pedicoccus, Enterococcus, Escherichia, Alcaligenes, Corynebacterium, Bacillus, Propionibacterium*, and combinations thereof;

at least one polymeric thickener;

at least about 50 wt. % of one or more ingredients with a sanitizing effect, the one or more ingredients with a sanitizing effect comprising alcohol, a quaternary ammonium compound, or a combination thereof; and up to about 30 wt. % water, wherein the sanitizing composition reduces pathogen binding on skin by a statistically significant amount, as compared to an otherwise identical sanitizing composition without the active ingredient.

2. The sanitizing composition of claim 1, wherein the one or more ingredients with a sanitizing effect is present in an amount above about 70 wt. %, based on the total weight of the sanitizing composition.

3. The sanitizing composition of claim 1, wherein the sanitizing composition comprises from about 0.05 wt. % to about 5.0 wt. % of the active ingredient, based on the total weight of the sanitizing composition.

4. The sanitizing composition of claim 1, wherein the sanitizing composition further comprises one or more skin conditioning agents.

5. The sanitizing composition of claim 4, wherein the one or more skin conditioning agents comprises one or more humectants, selected from the group consisting of propylene glycol, hexylene glycol, 1,4-dihydroxyhexane, 1,2,6-hexanetriol, sorbitol, butylene glycol, caprylyl glycol, propanediols, methyl propane diol, dipropylene glycol, triethylene glycol, glycerin (glycerol), polyethylene glycols, ethoxydiglycol, polyethylene sorbitol, glyceryl caprylate/caprate, and combinations thereof.

6. The sanitizing composition of claim 1, wherein the sanitizing composition further comprises one or more plug preventing additives in an amount up to about 20.0 wt. %, based on the total weight of the sanitizing composition.

7. The sanitizing composition of claim 1, wherein the sanitizing composition further comprises one or more moisturizing esters, selected from the group consisting of cetyl myristate, cetyl myristoleate, cetyl esters, diisopropyl sebacate, isopropyl myristate, and combinations thereof.

8. The sanitizing composition of claim 7, wherein the moisturizing ester is present in an amount up to about 10.0 wt. %, based on the total weight of the sanitizing composition.

* * * * *